(12) United States Patent  
Lee et al.

(10) Patent No.: US 9,035,075 B1
(45) Date of Patent: May 19, 2015

(54) CATALYST FOR ORGANIC REACTION AND METHOD OF USE THEREOF

(71) Applicant: RESEARCH & BUSINESS FOUNDATION SUNGKYUNKWAN UNIVERSITY, Suwon-si (KR)

(72) Inventors: Hyoyoung Lee, Suwon-si (KR); Youngmin Kim, Suwon-si (KR); Surajit Some, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 14/272,780

(22) Filed: May 8, 2014

(30) Foreign Application Priority Data

Oct. 25, 2013 (KR) .......................... 10-2013-0128107

(51) Int. Cl.
*C07C 201/12* (2006.01)
*B01J 21/18* (2006.01)
*C07D 333/22* (2006.01)

(52) U.S. Cl.
CPC ............... *C07C 201/12* (2013.01); *B01J 21/18* (2013.01); *C07D 333/22* (2013.01)

(58) Field of Classification Search
CPC ........................................................ C07C 201/12
USPC ............................................................... 549/76
See application file for complete search history.

(56) References Cited

FOREIGN PATENT DOCUMENTS

KR    1995-0013098 B1    10/1995

OTHER PUBLICATIONS

Su et al., Accounts of Chem. Res. (2013), vol. 46(10), pp. 2275-2285.*
Kim, Youngmin, et al. "Graphene oxide as a recyclable phase transfer catalyst." Chem. Commun. vol. 49 (2013): (21 pages).

* cited by examiner

*Primary Examiner* — Taofiq A Solola
(74) *Attorney, Agent, or Firm* — NSIP Law

(57) ABSTRACT

A catalyst for an organic reaction and a method of using a catalyst in an organic reaction are provided. The catalyst for an addition or condensation reaction includes a graphene oxide including an oxygen functional group, and the catalyst is configured to promote the addition or condensation reaction by bonding the oxygen functional group with an alkali metal ion or alkali earth metal ion during the addition or condensation reaction.

8 Claims, 22 Drawing Sheets

CATALYST FOR ORGANIC REACTION AND METHOD OF USE THEREOF

CROSS-REFERENCE TO RELATED APPLICATION

This application claims the benefit under 35 USC 119(a) of Korean Patent Application No. 10-2013-0128107 filed on Oct. 25, 2013, in the Korean Intellectual Property Office, the entire disclosure of which is incorporated herein by reference for all purposes.

BACKGROUND

1. Field

The following description relates to a catalyst for an organic reaction and a method for carrying out an organic reaction by using the catalyst, and to a phase transfer catalyst and a method of using the phase transfer catalyst.

2. Description of Related Art

Graphene and its derivatives hold great promise for diverse electronic applications, and have also attracted great interest for use in composite materials and catalysts due to their remarkable physical, chemical and electrical properties, including their very high specific surface area. As a part of a wider trend to develop green chemistry and to mimic nature, recent efforts have been made to develop aqueous organic-catalytic reactions [M. Raj and V. K. Singh, Chem. Commun., 2009, 6687]. Further, innovative synthetic approaches involving the use of chemicals that reduce risks to humans and the environment have gained interest. To this end, the development and use of catalysts that can be easily recovered and repeatedly recycled in a heterogeneous organic reaction system are of tremendous value.

In an organic synthesis reaction, a conventional phase transfer catalyst has been generally used in the manner that it catalyzes the reaction in the state that it is dissolved in an organic solvent. For this reaction, it is difficult to isolate only the catalyst from the solvent after the reaction is finished, and thus, there is limit in the ability to recycle the catalyst [Korean Patent No. 1995-0013098 B1]. Further, there is a disadvantage in that a given kind of a base must be used for the reaction.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a catalyst for an addition or condensation reaction, the catalyst including a graphene oxide comprising an oxygen functional group, in which the catalyst is configured to promote the addition or condensation reaction by bonding the oxygen functional group with an alkali metal ion or alkali earth metal ion during the addition or condensation reaction.

The catalyst may be a phase transfer catalyst capable of being recovered after the addition or condensation reaction and then being reused.

The oxygen functional group may include a member selected from the group consisting of an epoxy group, an alcohol group, a phenol group, a carbonyl group, a carboxyl group, a lactone group, a quinone group, and combinations thereof.

The alkali metal ion or alkali earth metal ion may include a cation of a metal selected from the group consisting of sodium, potassium, cesium, rubidium, manganese, calcium, strontium, barium, and combinations thereof.

The addition or condensation reaction may include a Michael addition reaction, an Aldol condensation reaction, a Claisen condensation reaction, or a Perkin reaction.

The Michael addition reaction may be performed by adding a Michael acceptor compound and a Michael donor compound.

The Michael donor compound may be represented by the following Formula (1):

wherein R or R' is each independently a $C_{1-12}$ alkyl group, a $C_{3-12}$ allyl group, a $C_{3-12}$ cycloalkyl group, a $C_{6-12}$ aryl group, a $C_{7-18}$ aralkyl group, a cyano group, a nitro group, an epoxide group, or a carbonyl group.

The Michael acceptor compound may include a member selected from the group consisting of an α, β-unsaturated carbonyl compound, an α, β-unsaturated nitrile compound, and combinations thereof.

In another general aspect, there is provided a method of using a catalyst including a graphene oxide including an oxygen functional group, the method involving: adding the catalyst to a reaction mixture for an addition or condensation reaction in the presence of a basic catalyst comprising an alkali metal ion or alkali earth metal ion, in which the addition or condensation organic reaction is promoted by bonding the oxygen functional group with the alkali metal ion or alkali earth metal ion.

The adding of the catalyst may involve dispersing the catalyst in an aqueous solvent that forms an aqueous phase of the reaction mixture.

The reaction mixture may include the aqueous phase and an organic phase.

The general aspect of the method may further include recovering the catalyst after the addition or condensation reaction and then reusing the catalyst.

The oxygen functional group may include a member selected from the group consisting of an epoxy group, an alcohol group, a phenol group, a carbonyl group, a carboxyl group, a lactone group, a quinone group, and combinations thereof.

The alkali metal ion or alkali earth metal ion may include a cation of a metal selected from the group consisting of sodium, potassium, cesium, rubidium, manganese, calcium, strontium, barium, and combinations thereof.

The addition or condensation reaction may include a Michael addition reaction, an Aldol condensation reaction, a Claisen condensation reaction, or a Perkin reaction.

The addition or condensation reaction may be a Michael addition reaction performed by adding a Michael acceptor compound and a Michael donor compound.

The Michael donor compound may be represented by the following Formula (1):

(1)

wherein R or R' is each independently a $C_{1-12}$ alkyl group, a $C_{3-12}$ allyl group, a $C_{3-12}$ cycloalkyl group, a $C_{6-12}$ aryl group, a $C_{7-18}$ aralkyl group, a cyano group, a nitro group, an epoxide group, or a carbonyl group.

The Michael acceptor compound may include a member selected from the group consisting of an α, β-unsaturated carbonyl compound, an α, β-unsaturated nitrile compound, and combinations thereof.

In another general aspect, there is provided a method of using a catalyst in an organic reaction, the method involving dispersing a catalyst comprising a graphene oxide comprising an oxygen functional group in an aqueous solvent, and forming a reaction mixture comprising an aqueous phase comprising a metal ion and the aqueous solvent and an organic phase comprising a first reactant and a second reactant, wherein the catalyst promotes a reaction between the first reactant and the second reactant by bonding the oxygen functional group with the metal ion.

The reaction may include a Michael addition reaction, an Aldol condensation reaction, a Claisen condensation reaction, or a Perkin reaction.

Other features and aspects will be apparent from the following detailed description, the drawings, and the claims.

Figure 1:
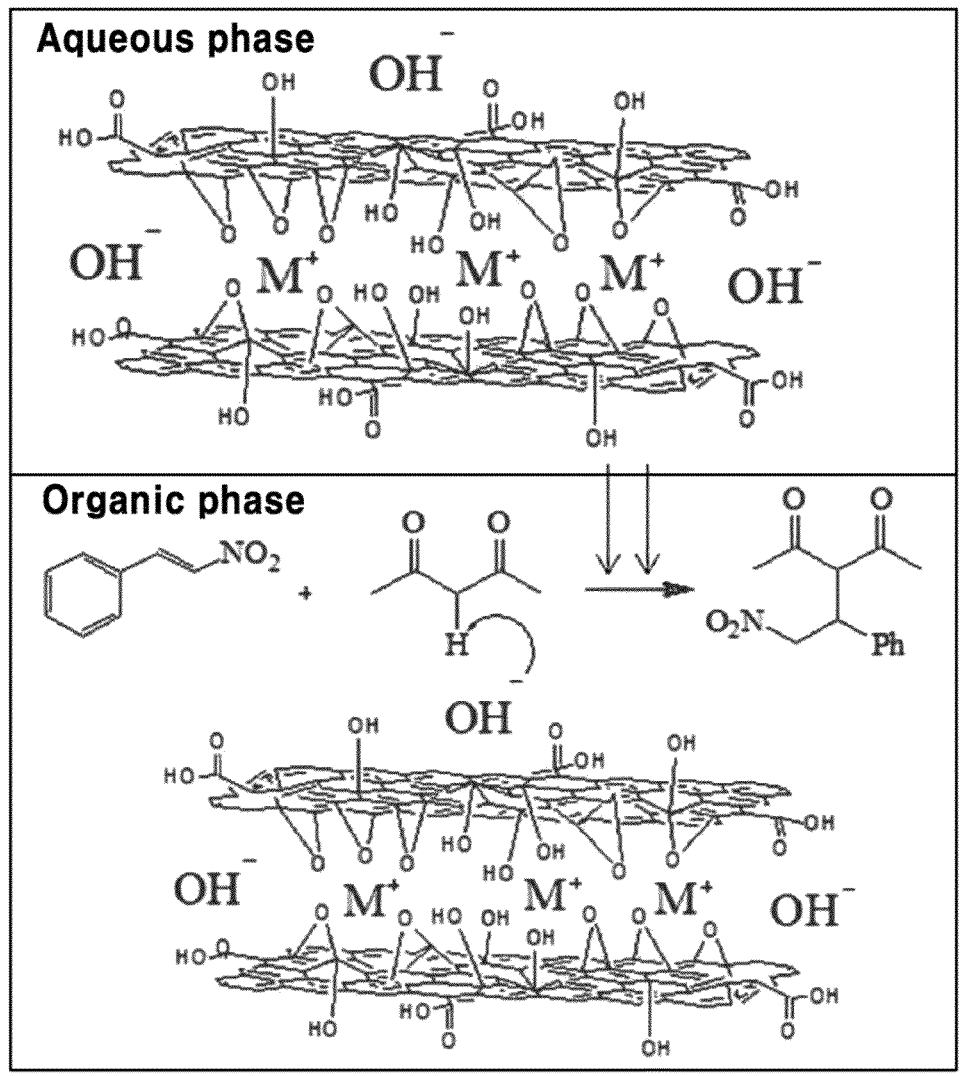
FIG. 1 is a schematic view illustrating a Michael addition reaction using an example of a phase transfer catalyst in accordance with the present disclosure.
Figure 2:
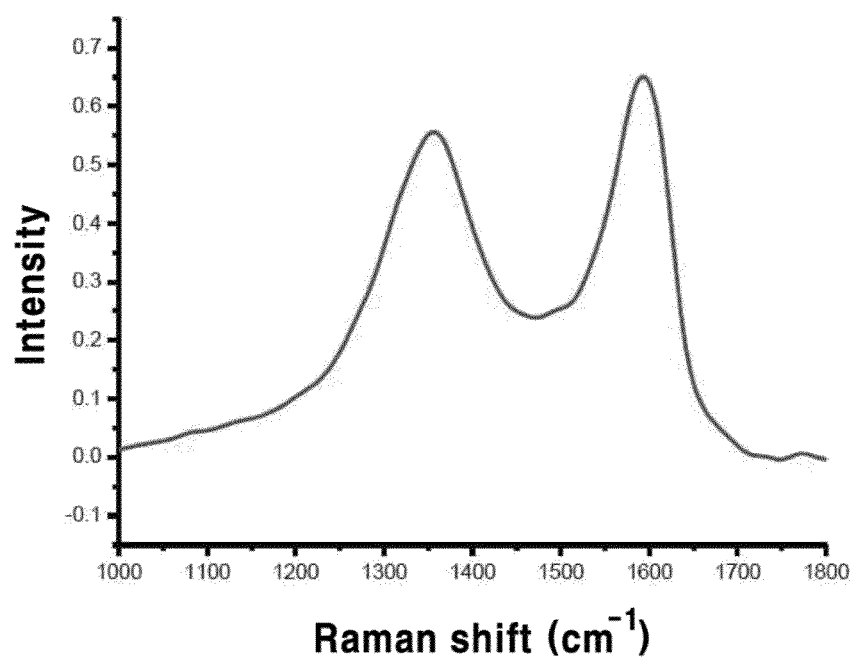
FIG. 2 illustrates a Raman spectrum of an example of graphene oxide in accordance with the present disclosure.
Figure 3:
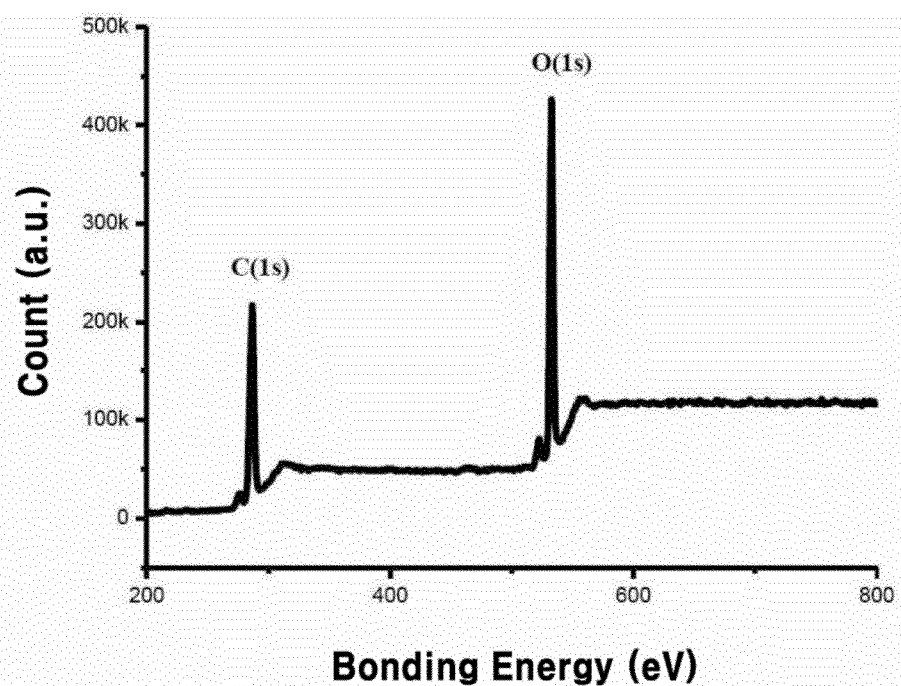
FIG. 3 illustrates an x-ray photoelectron spectroscopy (XPS) spectrum of an example of graphene oxide in accordance with the present disclosure.
Figure 4:
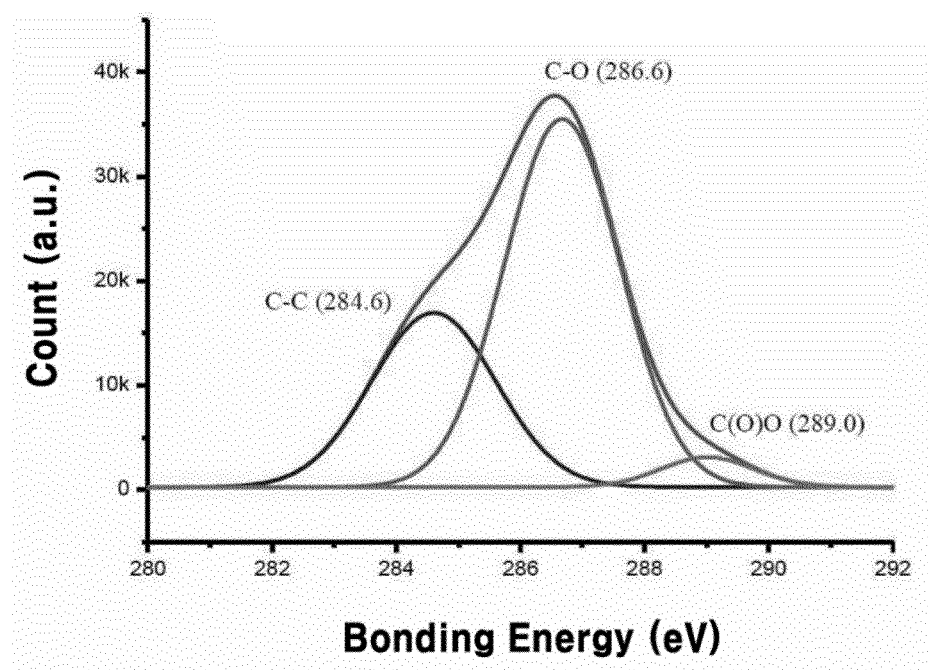
FIG. 4 illustrates a C1s spectrum of a high-resolution XPS of an example of graphene oxide in accordance with the present disclosure.
Figure 5:
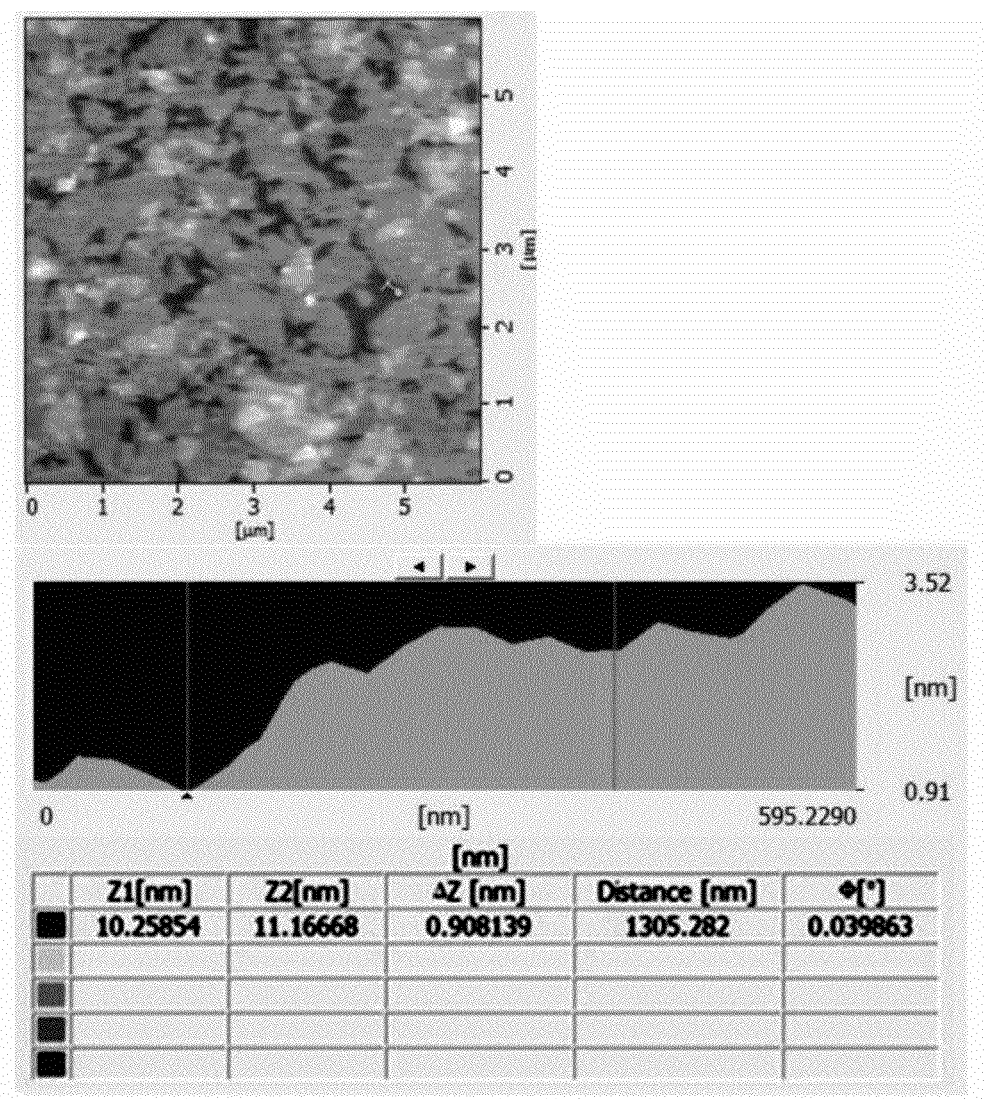
FIG. 5 illustrates an atomic force microscope (AFM) image of a graphene oxide in accordance with the present disclosure.
Figure 6:
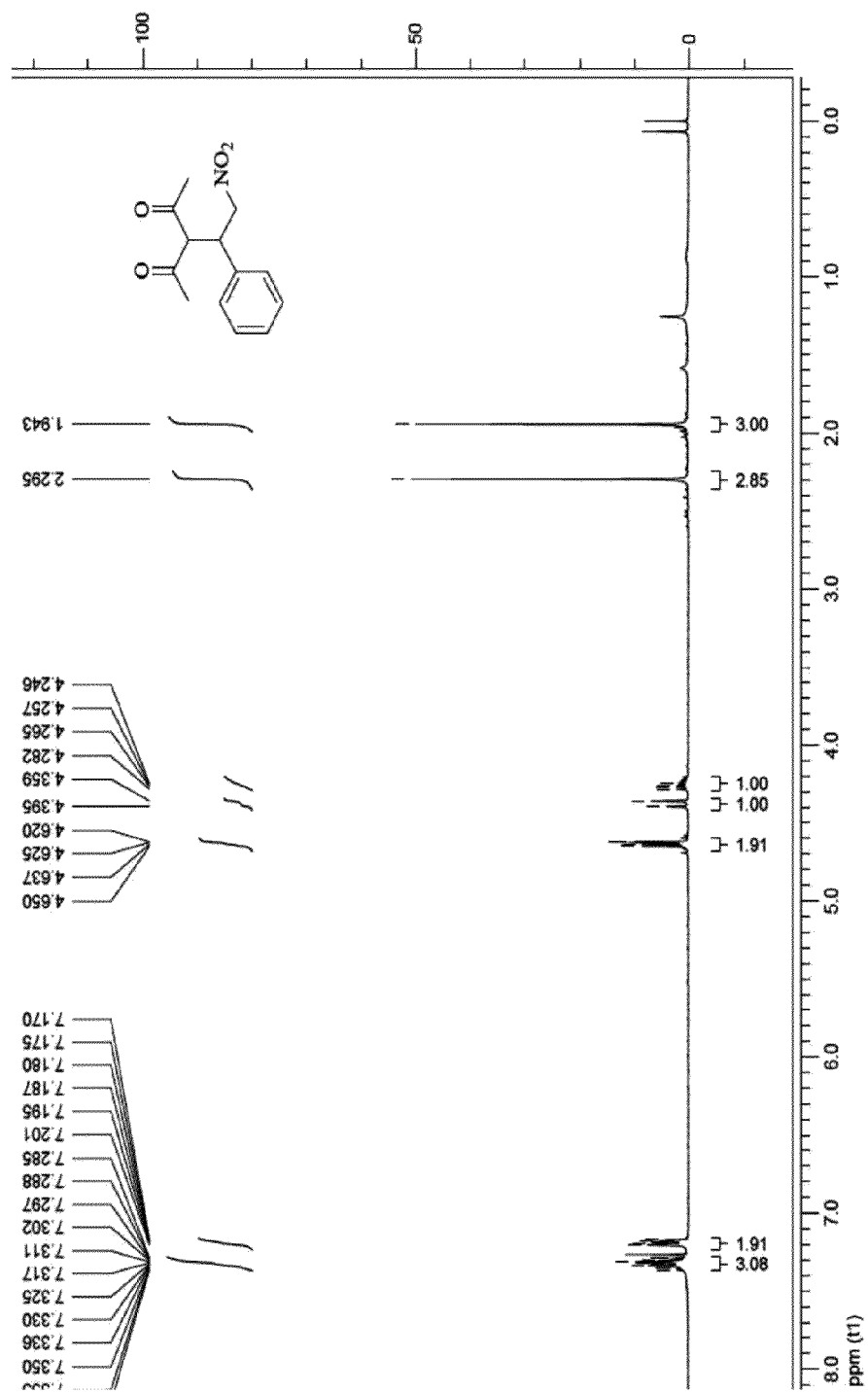
FIG. 6 illustrates a hydrogen-nuclear magnetic resonance ($^{1}$H-NMR) spectrum of a synthesized Michael addition reaction product 3a (Tables 1, and Entry 1 of Table 3) in accordance with the present disclosure.
Figure 7:
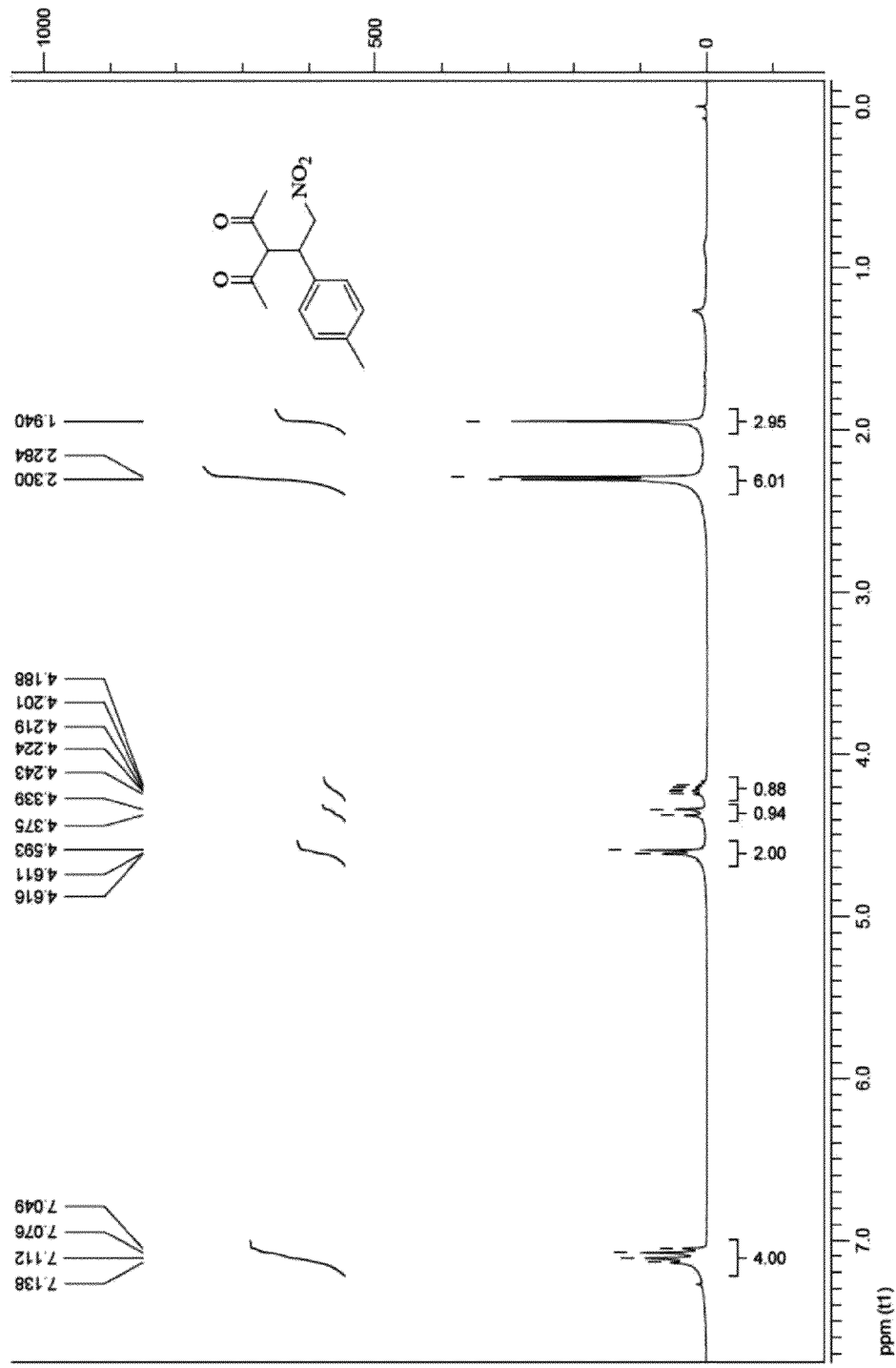
FIG. 7 illustrates a $^{1}$H-NMR spectrum of an example of a synthesized Michael addition reaction product 3b (Entry 2 of Table 3) in accordance with the present disclosure.
Figure 8:
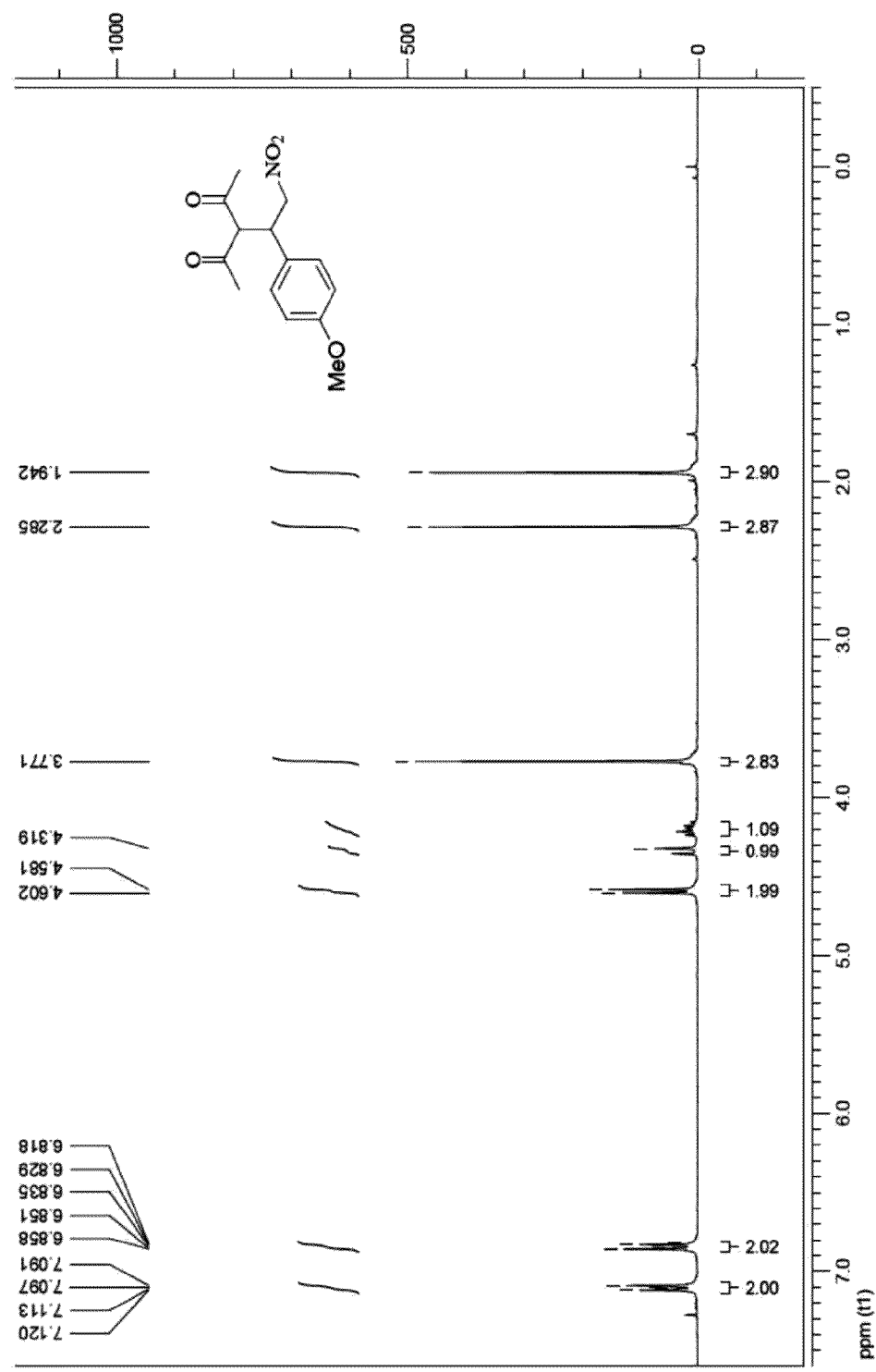
FIG. 8 illustrates a $^{1}$H-NMR spectrum of an example of a synthesized Michael addition reaction product 3c (Entry 3 of Table 3) in accordance with the present disclosure.
Figure 9:
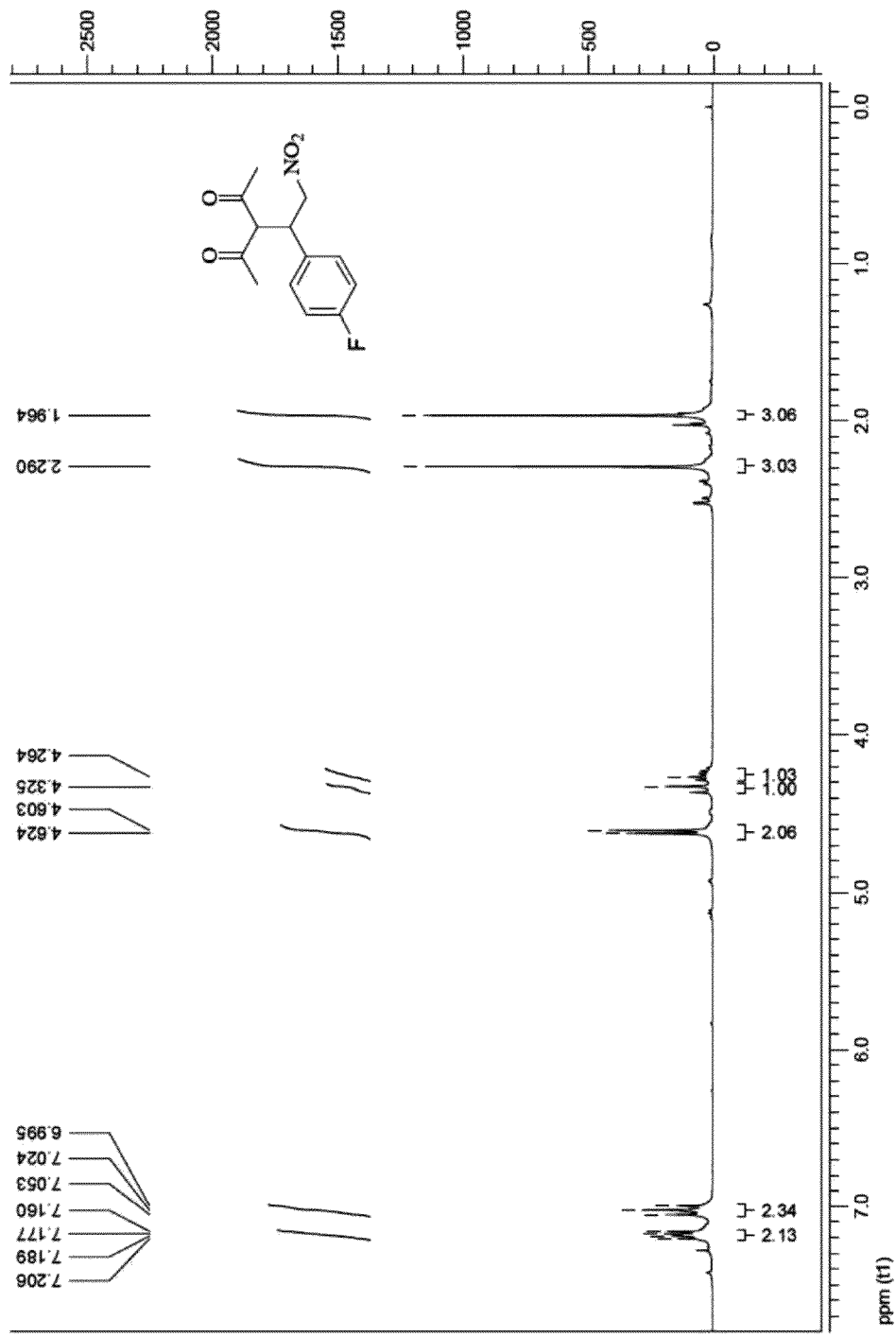
FIG. 9 illustrates a $^{1}$H-NMR spectrum of an example of a synthesized Michael addition reaction product 3d (Entry 4 of Table 3) in accordance with the present disclosure.
Figure 10:
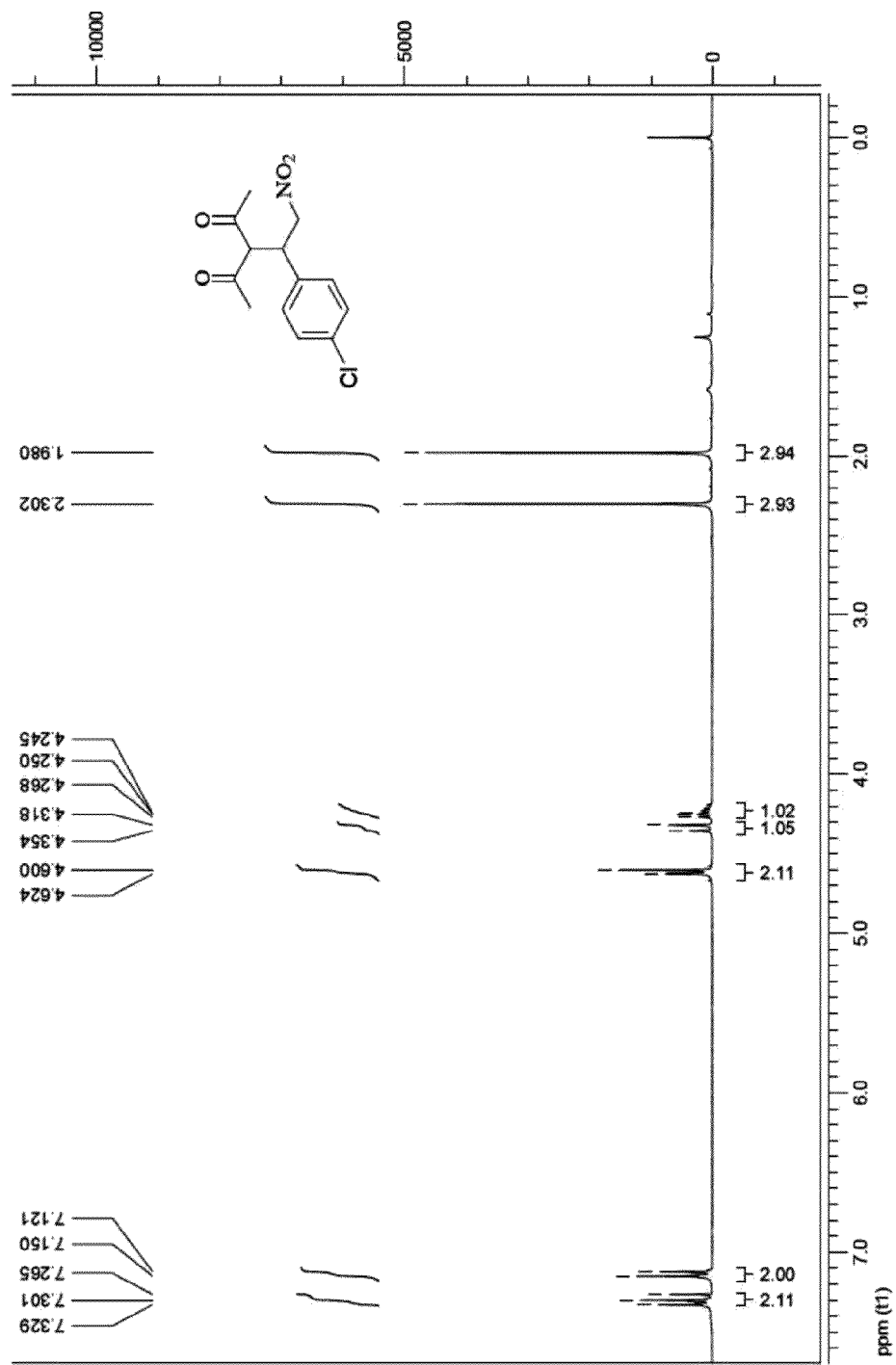
FIG. 10 illustrates a $^{1}$H-NMR spectrum of an example of a synthesized Michael addition reaction product 3e (Entry 5 of Table 3) in accordance with the present disclosure.
Figure 11:
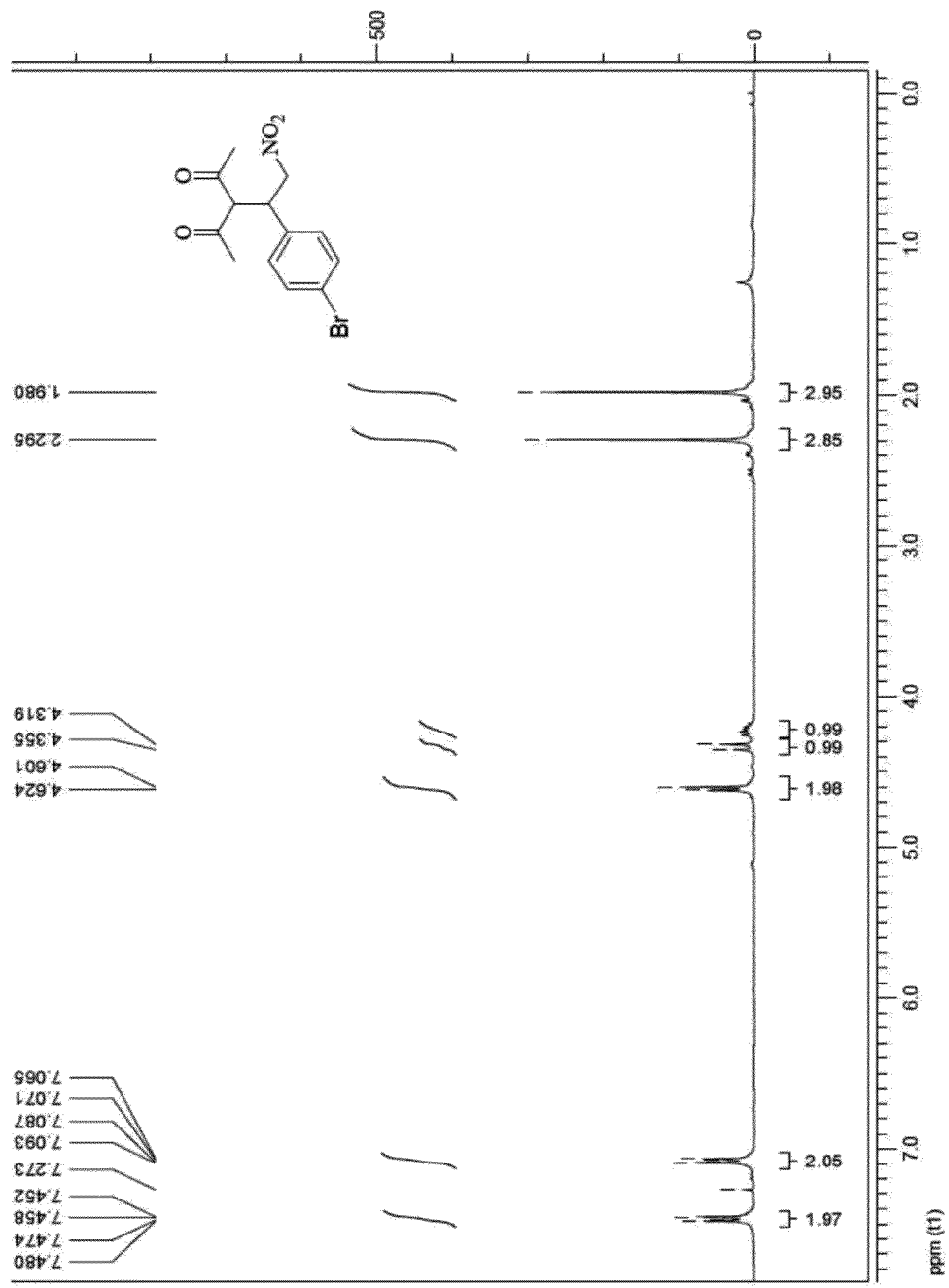
FIG. 11 illustrates a $^{1}$H-NMR spectrum of an example of a synthesized Michael addition reaction product 3f (Entry 6 of Table 3) in accordance with the present disclosure.
Figure 12:
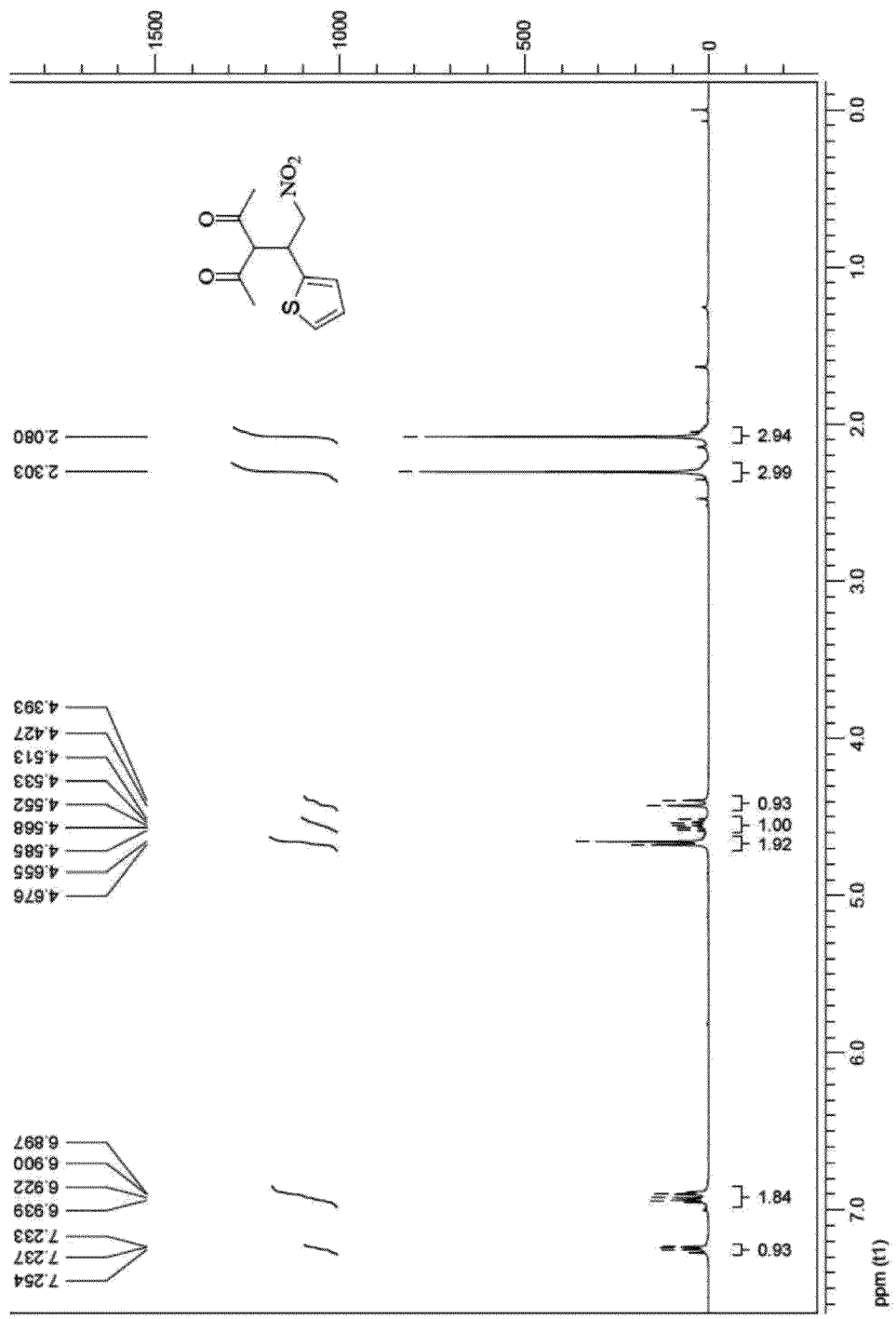
FIG. 12 illustrates a $^{1}$H-NMR spectrum of an example of a synthesized Michael addition reaction product 3g (Entry 7 of Table 3) in accordance with the present disclosure.
Figure 13:
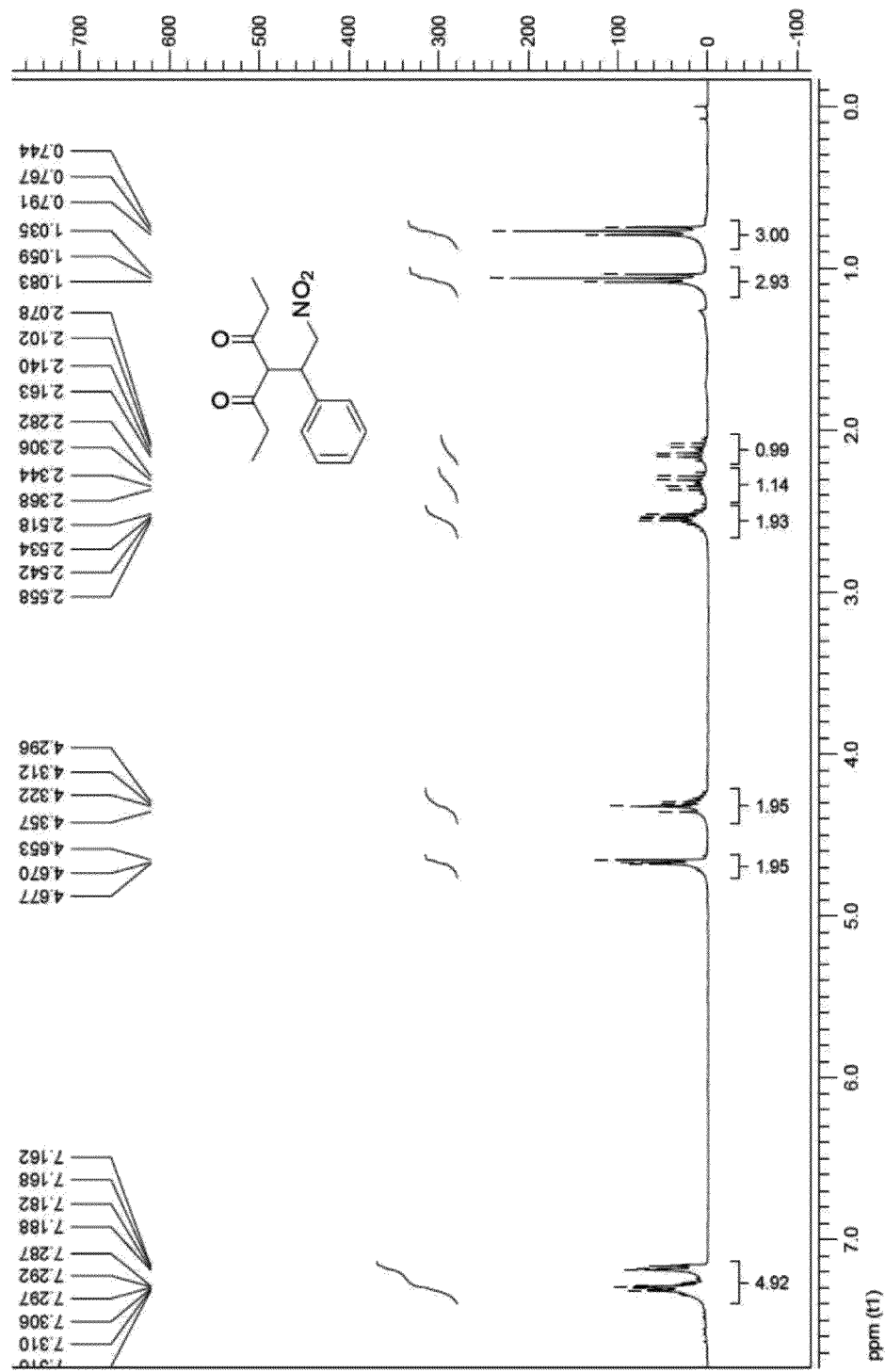
FIG. 13 illustrates a $^{1}$H-NMR spectrum of an example of a synthesized Michael addition reaction product 5a (Entry 1 of Table 4) in accordance with the present disclosure.
Figure 14:
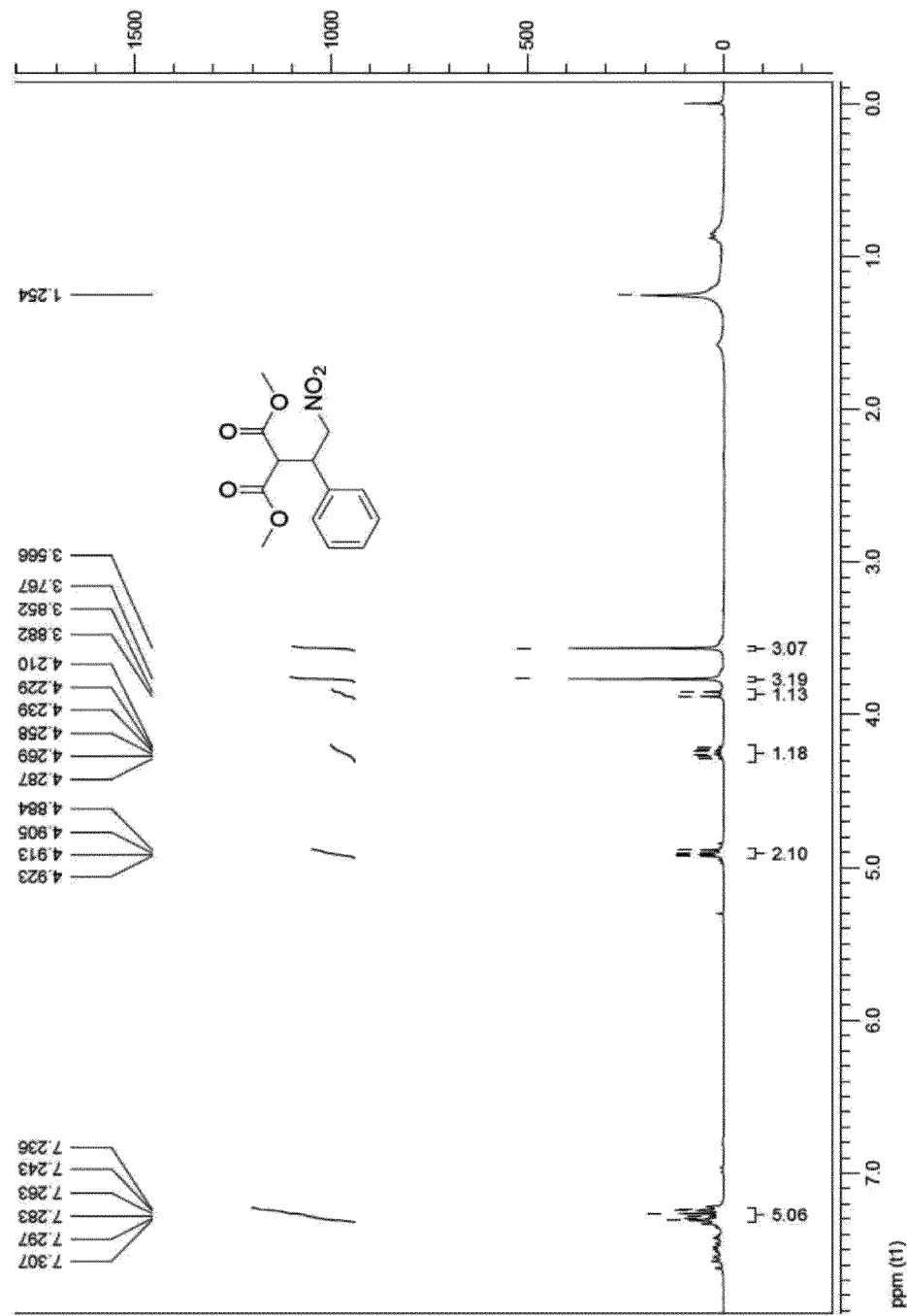
FIG. 14 illustrates a $^{1}$H-NMR spectrum of an example of a synthesized Michael addition reaction product 5b (Entry 2 of Table 4) in accordance with the present disclosure.
Figure 15:
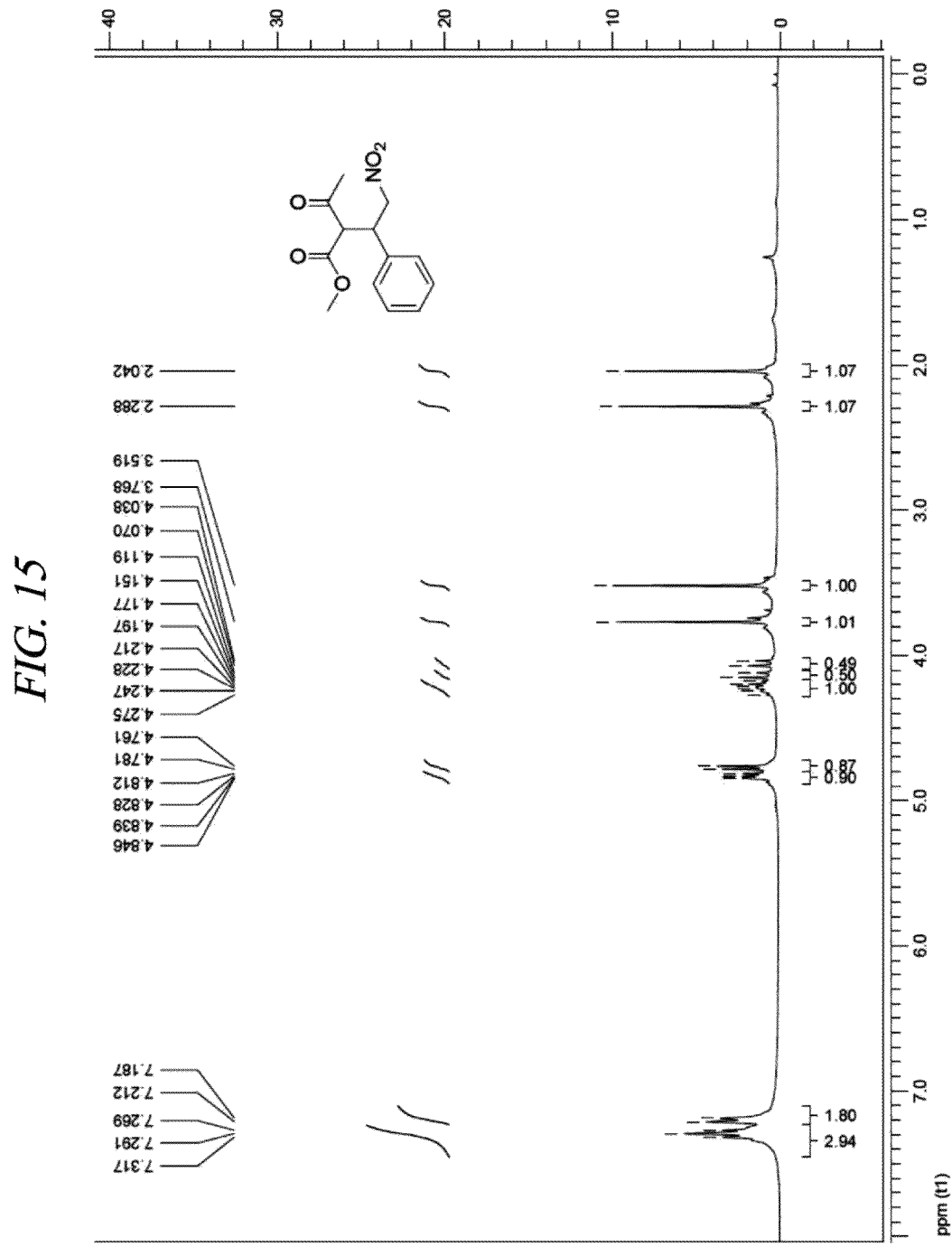
FIG. 15 illustrates a $^{1}$H-NMR spectrum of an example of a synthesized Michael addition reaction product 5c (Entry 3 of Table 4) in accordance with the present disclosure.
Figure 16:
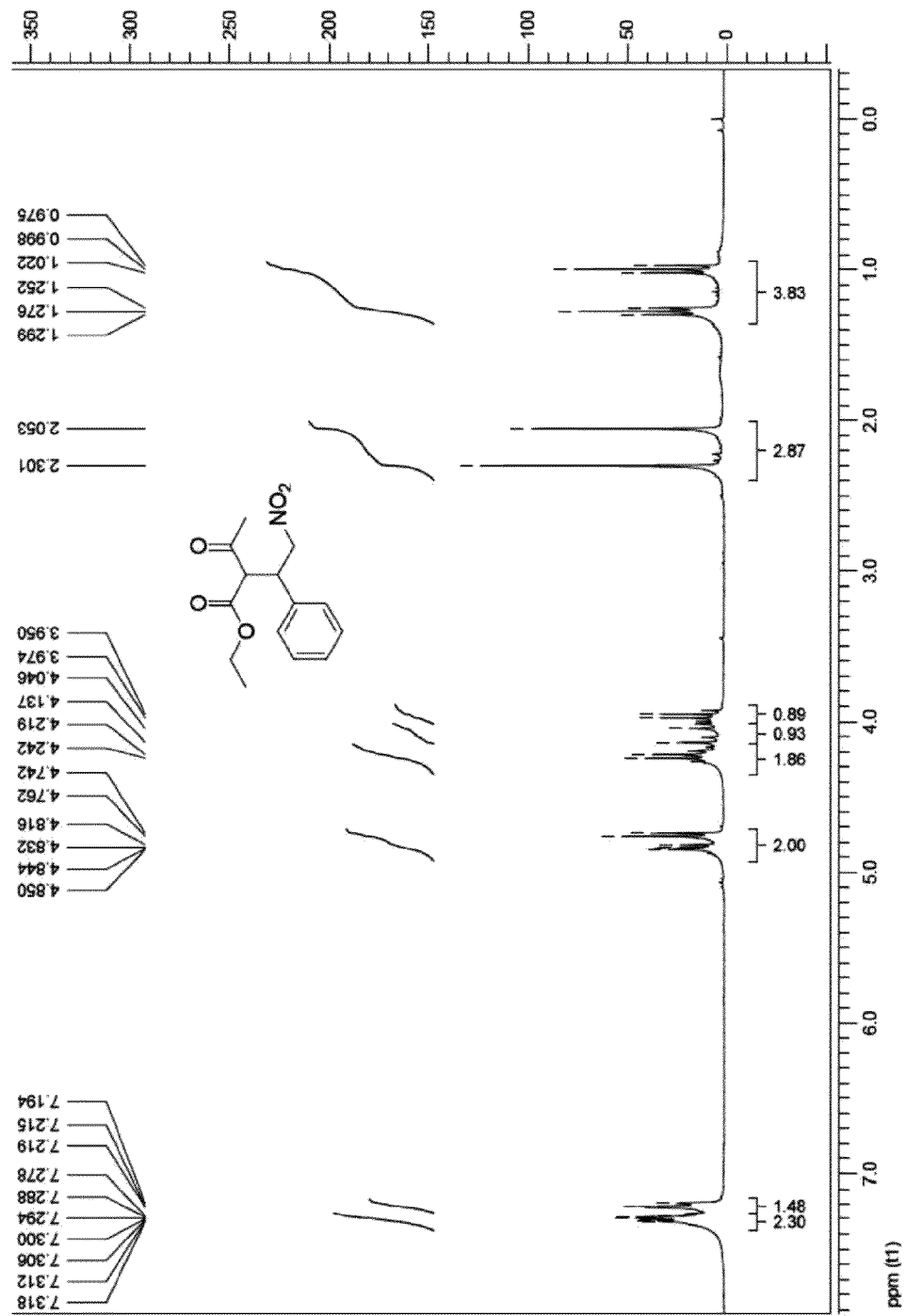
FIG. 16 illustrates a $^{1}$H-NMR spectrum of an example of a synthesized Michael addition reaction product 5d (Entry 4 of Table 4) in accordance with the present disclosure.
Figure 17:
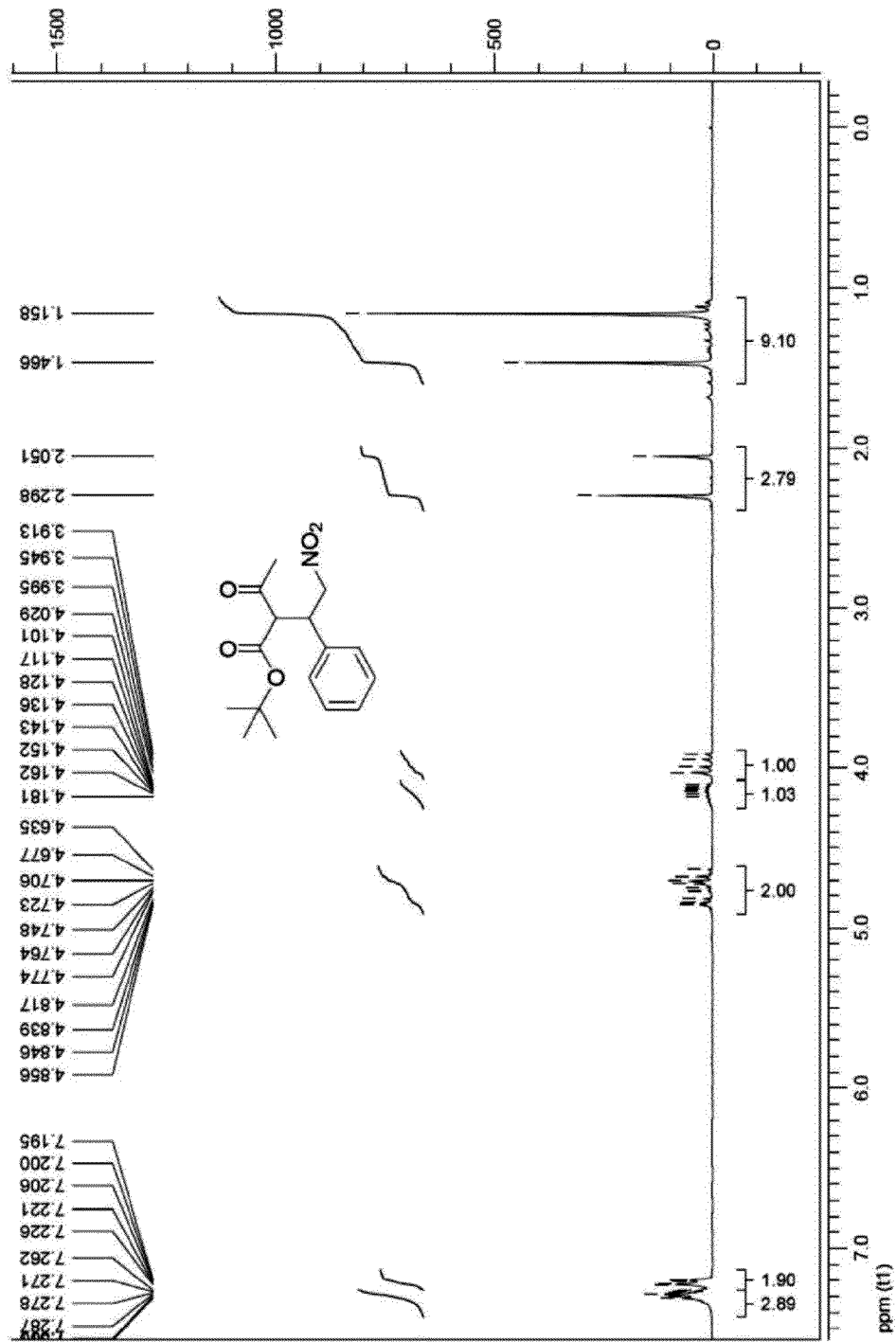
FIG. 17 illustrates a $^{1}$H-NMR spectrum of an example of a synthesized Michael addition reaction product 5e (Entry 5 of Table 4) in accordance with the present disclosure.
Figure 18:
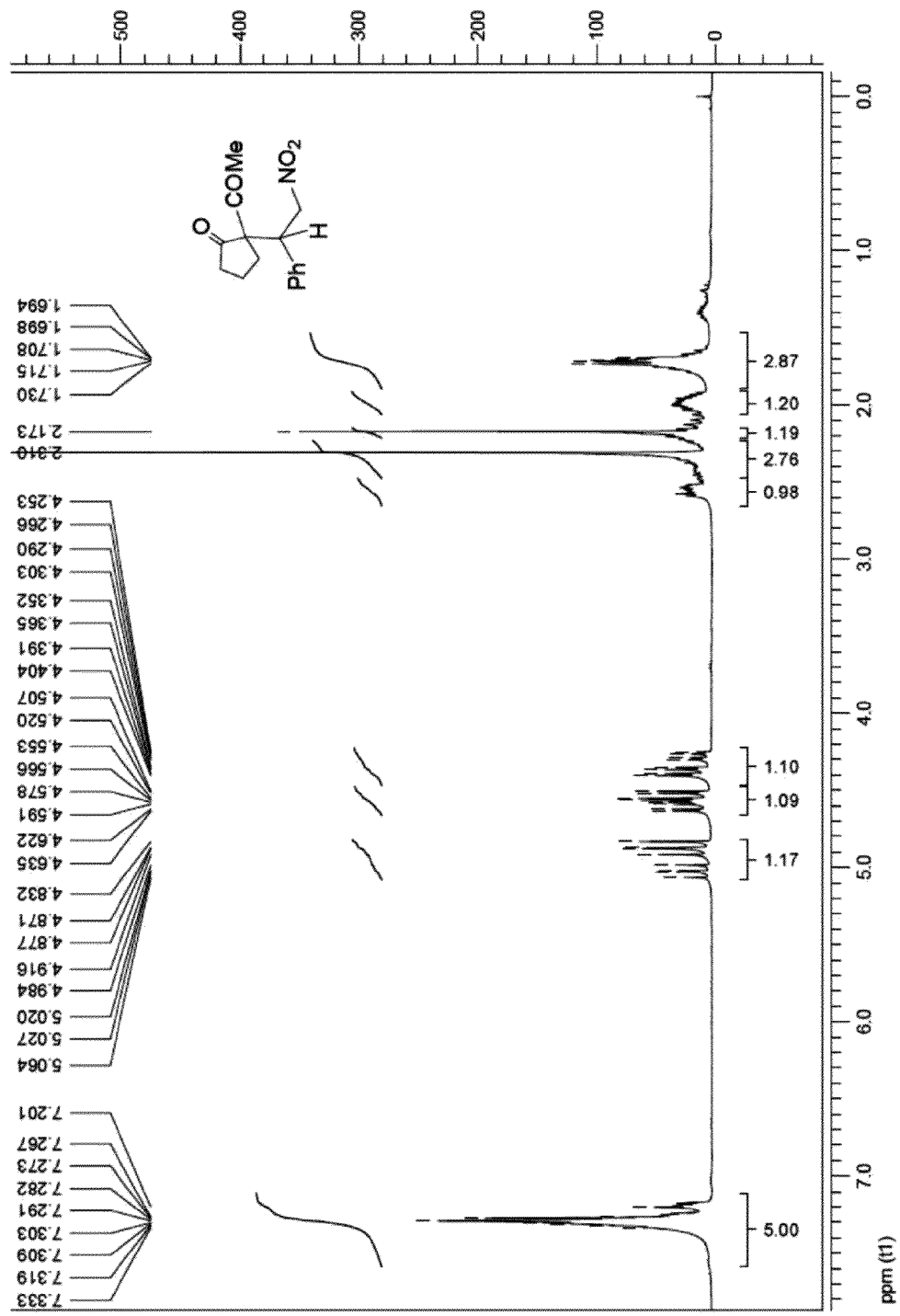
FIG. 18 illustrates a $^{1}$H-NMR spectrum of an example of a synthesized Michael addition reaction product 5f (Entry 6 of Table 4) in accordance with the present disclosure.
Figure 19:
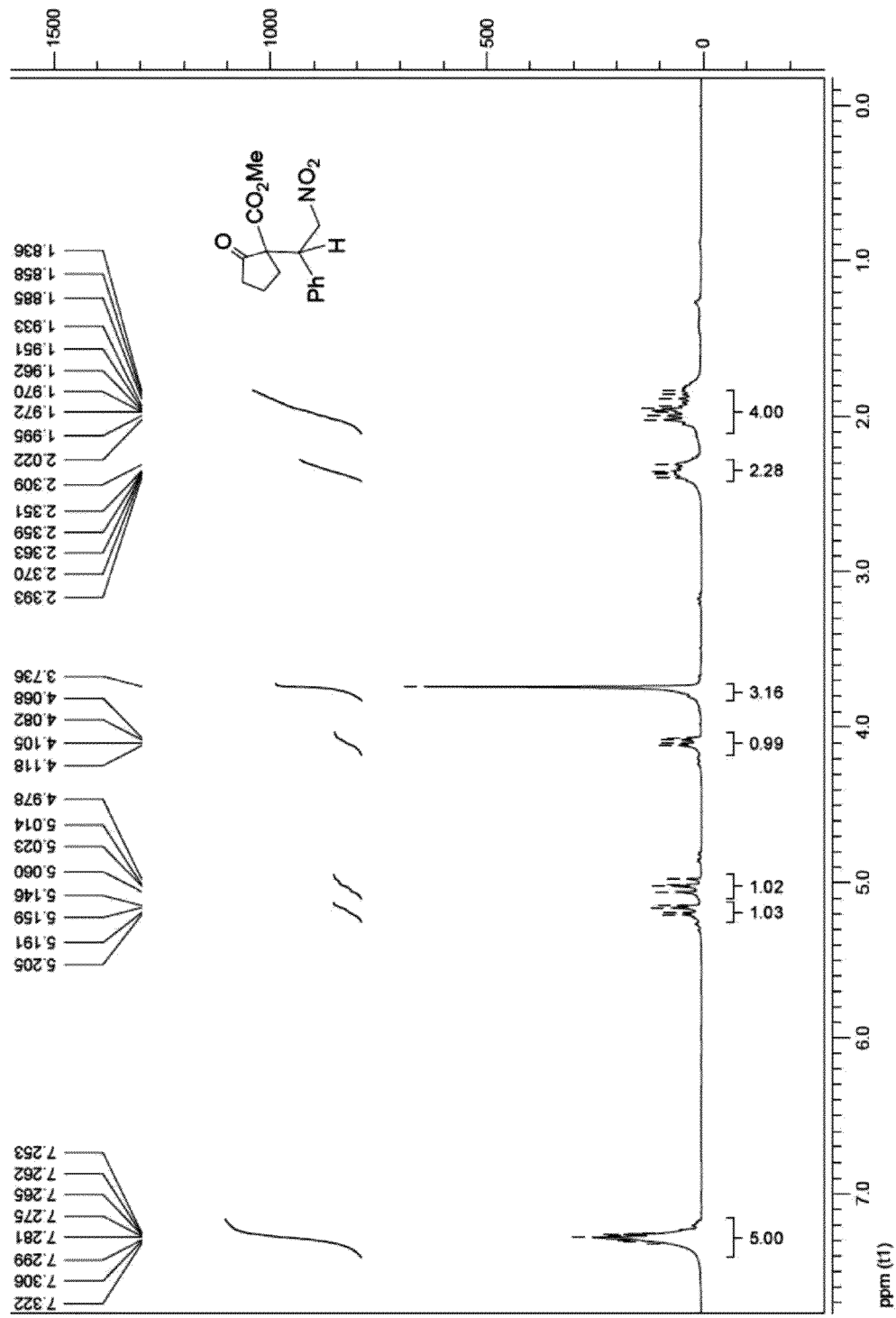
FIG. 19 illustrates a $^{1}$H-NMR spectrum of an example of a synthesized Michael addition reaction product 5g (Entry 7 of Table 4) in accordance with the present disclosure.
Figure 20:
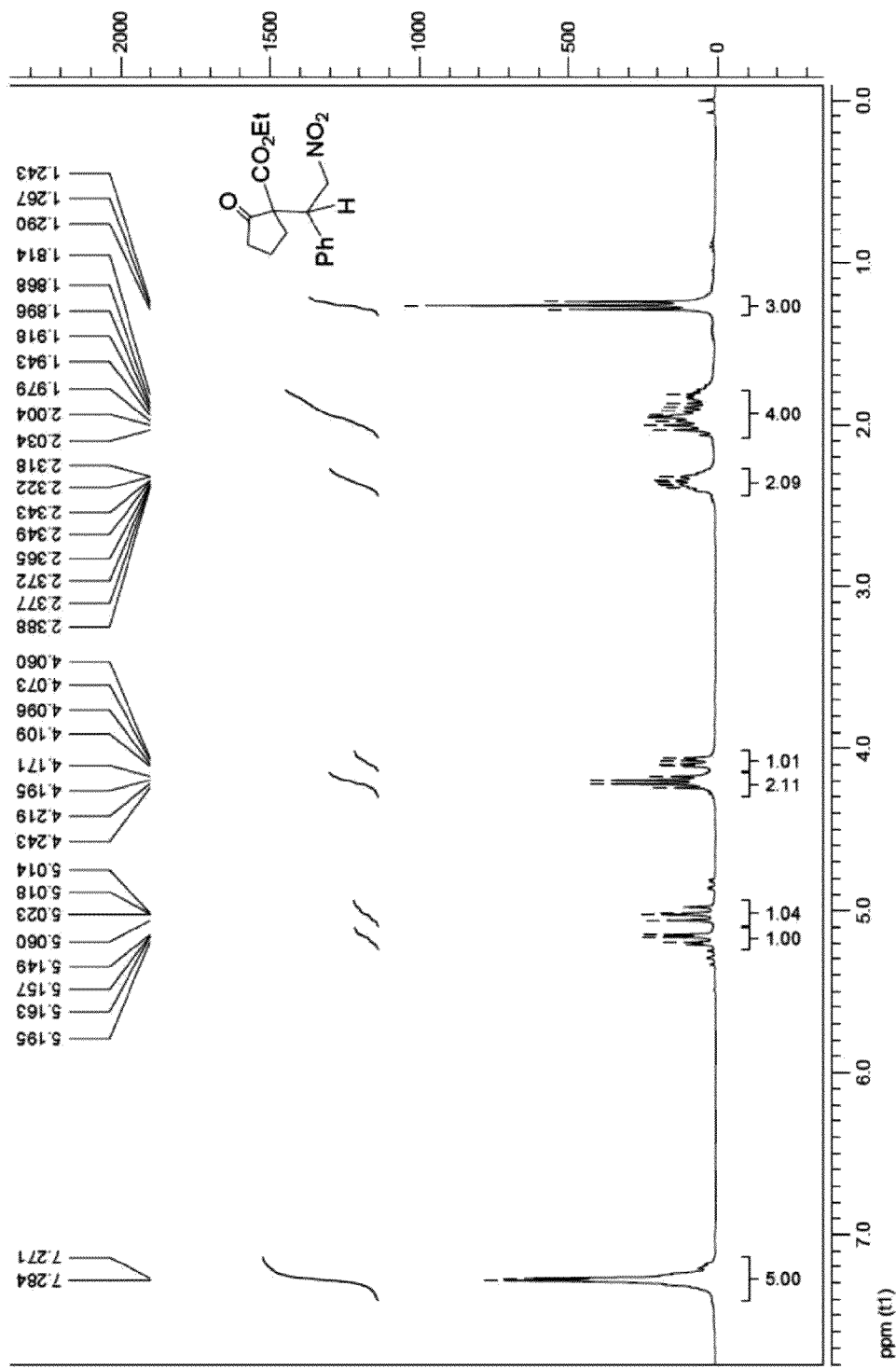
FIG. 20 illustrates a $^{1}$H-NMR spectrum of an example of a synthesized Michael addition reaction product 5h (Entry 8 of Table 4) in accordance with the present disclosure.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Throughout the present disclosure, the terms "connected to" or "coupled to" are used to designate a connection or coupling of one element to another element and include both a case where an element is "directly connected or coupled to" another element and a case where an element is "electronically connected or coupled to" another element via still another element.

The term "on" that is used to designate a position of one element with respect to another element includes both a case that the one element is adjacent to the another element and a case that any other element exists between these two elements.

The term "comprises or includes" and/or "comprising or including" used in the document means that one or more other components, steps, operations, and/or the existence or addition of elements are not excluded in addition to the described components, steps, operations and/or elements. Throughout the whole document, the terms "about or approximately" or "substantially" are intended to have meanings close to numerical values or ranges specified with an allowable error and intended to prevent accurate or absolute numerical values disclosed for understanding of the present invention from being illegally or unfairly used by any unconscionable third party. Through the whole document, the term "step of" does not mean "step for."

The term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

The expression "A and/or B" means "A or B, or A and B."

The term "graphene" means that multiple carbon atoms are bonded to one another through covalent bond, thereby forming polycyclic aromatic molecules, and the carbon atoms bonded through the covalent bond form a six (6) circular ring as a basic repeat unit, but may further include five (5) and/or seven (7) circular rings. Accordingly, a sheet formed of the graphene appears to be a monolayer of the covalently bonded carbon atoms, but may not be limited thereto. The sheet formed of the graphene may have various structures, and the structures may vary depending on a content of the 5 and/or 7 circular rings that may be contained in the graphene. Furthermore, if the sheet formed of the graphene is a monolayer, it may be stacked on one another thereby forming multiple layers, and a side end part of the graphene sheet may be saturated with hydrogen atoms, but may not be limited thereto.

The terms "graphene oxide" may be abbreviated as "GO." The graphene oxide may include a structure, in which a functional group containing oxygen such as a carboxyl group, a hydroxyl group or an epoxy group is bonded on monolayer graphene, but may not be limited thereto.

Hereinafter, various examples are described in detail. However, the present disclosure is not limited thereto.

In an example embodiment, a phase transfer catalyst for an addition or condensation organic reaction that functions in the presence of a basic catalyst including an alkali metal ion or alkali earth metal ion is provided. In this example, the phase transfer catalyst includes a graphene oxide containing an oxygen functional group, and the addition or condensation organic reaction is promoted by bonding the oxygen functional group of the phase transfer catalyst with the alkali metal ion or alkali earth metal ion during the addition or condensation organic reaction.

In accordance with one example embodiment, the phase transfer catalyst may be recovered and reused after the organic reaction. However, the phase transfer catalyst is not limited thereto. For example, the phase transfer catalyst may be recovered and reused through a process including filtering the solvent, and washing, or drying the phase transfer catalyst after the organic reaction; however, the present disclosure is not limited thereto.

In accordance with one example embodiment, the oxygen functional group may include a member selected from the group consisting of an epoxide group, an alcohol group, a phenol group, a carbonyl group, a carboxyl group, a lactone group, a quinone group, and combinations thereof; however, the present disclosure is not limited thereto.

In accordance with one example embodiment, the alkali metal ion or the alkali earth metal ion may include a cation of a metal selected from the group consisting of sodium, potassium, cesium, rubidium, manganese, calcium, strontium, barium and combinations thereof; however, the present disclosure is not limited thereto.

In accordance with one example embodiment, the phase transfer catalyst including a graphene oxide may speed up the reaction to provide a faster reaction and may result in a higher yield because the graphene oxide has a large area with many oxygen functional groups. For example, the performance of the phase transfer catalyst including a graphene oxide would exceed that of the best-known crown ether (CE) in the organic reaction. Accordingly, the organic reaction using the graphene oxide phase transfer catalyst can provide a faster reaction and a higher yield than the organic reaction using the crown ether catalyst. The oxygen functional groups are expected to easily hold the alkali metal or alkali earth metal cations by forming a metal-centered intercalated structure like graphene oxide-metal-graphene oxide layers. Furthermore, because the graphene oxide carries many oxygen functional groups throughout its surface layer, the intercalated structure would accommodate alkali metal or alkali earth metal cations of any size, including $Na^+$, $K^+$ and $Cs^+$.

In accordance with one example embodiment, the organic reaction may include a Michael addition reaction, an Aldol condensation reaction, a Claisen condensation reaction or a Perkin reaction; however, the present disclosure is not limited thereto.

The Michael addition reaction is a known chemical reaction, in which a Michael acceptor reacts with a Michael donor to extend carbon chains. The Michael addition reaction is one of the most useful and representative methods for formation of new C—C bonds. The formation of new C—C bonds via the Michael addition reaction is an important transformation in organic chemistry, and is used extensively in the synthesis of a variety of molecules, including biologically active natural products and antibiotics.

In accordance with one example embodiment, the Michael addition reaction may be a reaction, in which a compound containing a Michael acceptor and a compound including a Michael donor are added and reacted with each other; however, the present disclosure is not limited thereto.

In the Michael addition reaction, the Michael acceptor reacts with the Michael donor to extend carbon chains, and the Michael donor is a compound having a functional group containing at least one Michael active hydrogen atom, which is a hydrogen atom adhered to a carbon atom positioned between two electron withdrawing groups like C═O and/or C≡N, i.e., a Michael donor functional group.

In accordance with one example embodiment, the compound containing the Michael donor, or the Michael donor compound, may include a compound represented by Chemical Formula 1 below, but the compound is not limited thereto:

[Chemical Formula 1]

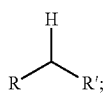

In Chemical Formula 1, R or R' is independently an alkyl group having 1 to 12 carbons, an allyl group having 3 to 12 carbons, a cycloalkyl group having 3 to 12 carbons, an aryl group having 6 to 12 carbons, an aralkyl group having 7 to 18 carbons, a cyano group, a nitro group, an epoxide group, or a carbonyl group; and the Michael donor functional group may include a member selected from the group consisting of, for example, 2,4-pentanedione, a 1,3-dicarbonyl compound, acetoacetate, and acetoacetamide, which have one Michael donor functional group per molecule; methyl acetoacetate, t-butyl acetoacetate, allyl acetoacetate, 2-ethylhexyl acetoacetate, lauryl acetoacetate, and 2-acetoacetoxyethyl methacrylate, which have two Michael donor functional groups per molecule; 1,4-butandiol diacetoacetate, 1,6-hexandiol diacetoacetate, neopentyl glycol diacetoacetate, and cyclohexane dimethanol diacetoacetate, which have 4 Michael donor functional groups per molecule; N,N-dimethylacetoacetateamide, methyl cyanoacetate, ethyl cyanoacetate, and butyl cyanoacetate, which have 8 Michael donor functional groups per molecule; and combinations thereof, but may not be limited thereto.

In accordance with one example embodiment, the compound containing the Michael acceptor, or the Michael acceptor compound, is a monomer or polymer having a Michael acceptor functional group. Any compound known in the art to be useful for the Michael addition reaction can be used without limitation. For example, the Michael acceptor compound may include a member selected from the group consisting of an α, β-unsaturated carbonyl compound, an α, β-unsaturated nitryl compound, and combinations thereof, and may specifically include an α, β-unsaturated carbonyl compound such as a maleimide derivative, a maleic acid ester derivative, a fumaric acid ester derivative, or a (metha) acrylate derivative; trans β-nitro olefin, or trans β-nitro styrene, but may not be limited thereto.

The Aldol condensation reaction polymerizes bimolecular aldehyde or ketone in the presence of a base to produce β-hydroxy aldehyde or ketone. In one example embodiment, the Aldol condensation reaction using the catalyst including a graphene oxide may be, for example, a reaction represented by Reaction Formula 1 below; however, the disclosure is not limited thereto:

[Reaction Formula 1]

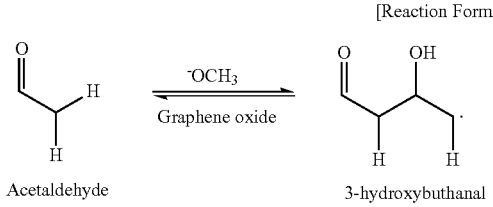

The Claisen condensation reaction is a reaction, in which one ester is condensed with one ester or one ketone in the presence of a base to produce a β-keto ester or β-diketone. In one example embodiment, the Claisen condensation reaction using the catalyst including a graphene oxide may be, for example, a reaction represented by Reaction Formula 2 below; however, the disclosure is not limited thereto:

[Reaction Formula 2]

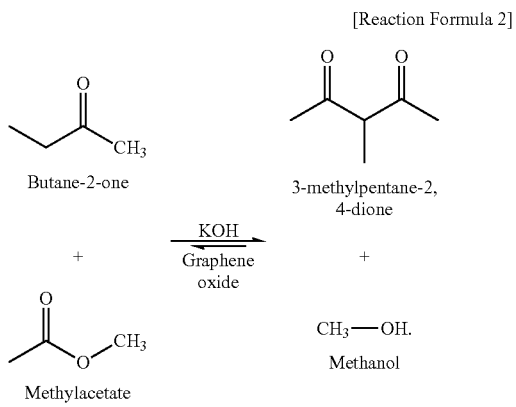

A Perkin reaction is a reaction, in which an aromatic aldehyde and a carboxylic anhydride are condensed with each other in the presence of a base to produce an α, β-unsaturated carboxylic acid. In one example embodiment, a Perkin reaction using a catalyst including a graphene oxide may be, for example, a reaction presented by Reaction Formula 3 below; however, the disclosure is not limited thereto:

[Reaction Formula 3]

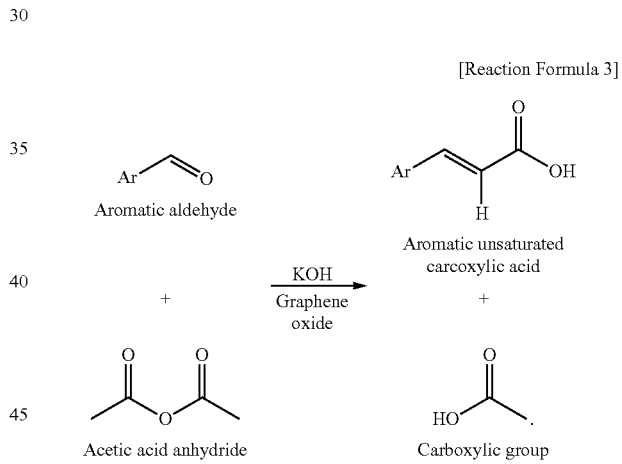

Graphene oxide does not dissolve in water or organic solvents such as methylene chloride (MC); however, it is possible to disperse graphene oxide in aqueous solvents or metyl chloride to obtain of a graphene oxide solution. The dispersion may be a uniform dispersion, or a substantially uniform dispersion. The insolubility of the graphene oxide has been a serious drawback in other applications; however, as a phrase transfer catalyst, the graphene oxide is expected to exhibit a strong advantage. After the reaction is completed, for example, the phase transfer catalyst including the graphene oxide may be collected and reused simply by filtering the solvent, washing and drying the filtrate; however, the disclosure is not limited thereto. For example, after the Michael addition reaction is completed, the graphene oxide may be collected simply by filtering, washing, and drying the graphene oxide-metal composites. The characteristics of graphene oxide such as its insolubility is superior to that of crown ether, which is not easily recovered after the organic reaction is over due to its high solubility.

In accordance with one example embodiment, the organic reaction may be carried out in the presence of an organic solvent, and any suitable organic solvent known in the art may be used without limitation. For example, the organic solvent may include methylene chloride, 2-methyl tetrahydrofuran, methanol, ethanol, dimethylsulfoxide or others; however, the solvents that may be used for the organic reaction is not limited thereto.

Hereinafter, the example embodiment is described in more detail by using Examples. The Examples are provided for illustrative purposes and to further the understanding of various example embodiments. The present disclosure is not limited to the Examples.

EXAMPLES

<Production and Characterization of Graphene Oxide>

Graphene oxide (GO) was prepared from natural graphite powder by applying a modified Hummer's method using sulfuric acid, potassium permanganate, and sodium nitrate, and was purified, in accordance as previously reported in [I. K. Moon, J. Lee, R. S. Ruoff and H. Lee, Nat. Commun., 2010, 1, 73]. As reported, it was identified that abundant oxygen functional groups were present at both edges and defects in the plane of the graphene oxide sheet. The abundant oxygen functional groups of the graphene oxide may function as key elements to act as cation holders, which make bases and hydroxide anions stronger, and also may make the reaction related to the high surface areas faster to enhance the activities. The possible reaction process is illustrated in FIG. 1. FIG. 1 illustrates a Michael addition reaction that uses an example of a phase transfer catalyst including a graphene oxide. As illustrated, the graphene oxide is first dispersed in an aqueous phase in the presence of metal ions, to facilitate the transfer of the metal ion catalysts to an organic phase in which the addition reaction between the first reactant and the second reactant occurs.

For efficient catalytic performance, graphene oxide nanosheets need to be fully dispersed in the reaction medium in order to maximize the number of catalytic sites provided by various oxygen functional groups, especially epoxy and hydroxyl groups. XPS, Raman and AFM analysis were used to characterize the graphene oxide in FIG. 2 to FIG. 5.

<Materials and Characterization Analysis>

All chemicals used in this Example were obtained from commercial sources and used without further purification. The organocatalysts examined in this Example were prepared according to a literature procedure described in [I. K. Moon, J. Lee, R. S. Ruoff and H. Lee, Nat. Commun., 2010, 1, 73]. The chromatographic purification of the products was conducted by flash chromatography using Merck silica gel 60 (230-400 mesh). Thin-layer chromatography was conducted on Merck silica gel 60F plates. Natural graphite (Bay Carbon, SP-1 graphite), sulfuric acid (95%-97%), hydrogen peroxide (30 wt. %), potassium permanganate, sodium nitrate, potassium hydroxide, sodium hydroxide, and cesium hydroxide were obtained from commercial sources and used as received. Raman spectroscopy measurements were taken using a micro-Raman system (Renishaw, RM1000-In Via) with an excitation energy of 2.41 eV (514 nm). X-ray photoemission spectroscopy (XPS) measurements were made by a SIGMA PROBE (ThermoVG, U.K.) with a monochromatic Al—Kα X-ray source at 100 W.

<Carrying Out Michael Addition Reaction>

Graphene oxide (GO) was dispersed in deionized water to make a solution having a graphene oxide concentration of 0.5 mg/mL. A solution of potassium hydroxide (10.3 mg, 1.1 equiv.) was added as a base to 0.5 mL of the graphene oxide solution. Subsequently, the graphene oxide solution, to which potassium hydroxide was added, was added to a methylene chloride (MC) solution, which included reactants in a 5 mL vial, trans-β-nitrostyrene (1a of Tables 1, 3 and 4, 25 mg, 0.1676 mmol, 1 equiv.), and 2,4-pentanedione (2 of Tables 1 and 3, 0.03 mL, 1.5 equiv.). The methyl chloride solution, which included the reactants, the graphene oxide, and the base (KOH, NaOH, or CsOH), was vigorously stirred by using one magnetic bar at a stirring speed of 900 rpm at a room temperature. Completion of the reaction was monitored by TLC. After an aqueous HCl solution (1 N, 1 mL) was added to quench the reaction, a product of the reaction was extracted with $CH_2Cl_2$ (3×5 mL). The product of the reaction was washed with water and dried over anhydrous sodium sulfate ($Na_2SO_4$), and the solvent was concentrated. The obtained crude product was purified by column chromatography on silica gel to obtain the Michael addition reaction product 3a illustrated in Tables 1 and 3. After the reaction was over, the used graphene oxide was recovered by performing a simple filtration and washing the filtrate with methyl chloride, using a nylon membrane filter having a 0.45 μm pore size. Subsequently, in order to recover the graphene oxide, the filtered and washed graphene oxide was dried by a vacuum desiccator for several hours.

<Characteristics of the Catalyst Including the Graphene Oxide Through the Michael Addition Reaction>

The as-made graphene oxide was dispersed in water to create an aqueous solution. The electrostatic repulsion among negatively charged carboxylate groups on the edges of the graphene oxide sheet prevented aggregation and stabilized the dispersion. In this way, most of the surface area of each single-layer graphene oxide sheet was available to provide catalytic reaction sites. After the graphene oxide solution was prepared, one of the three bases (KOH, NaOH and CsOH) containing alkali metal ions was dissolved in the graphene oxide solution for each individual experiment. Subsequently, the graphene oxide solution, in which each of the bases was dissolved, was added to a reaction mixture of trans-β-nitrostyrene and 2,4-pentanedione in a methyl chloride solvent or other derivative systems. All experiments were carried out at a room temperature, and reactants were vigorously stirred. To evaluate the graphene oxide catalyst of the Michael addition reaction, 2,4-pentanedione as a nucleophile and trans-β-nitrostyrene as an electrophile, using 0.5 mL of an aqueous solution containing 0.5 mg/mL of the graphene oxide catalyst and 1 mL of the methyl chloride solvent, were used at a room temperature (Table 1).

TABLE 1

Michael addition reaction of trans-β-nitrostyrene and 2,4-pentanedione[a]

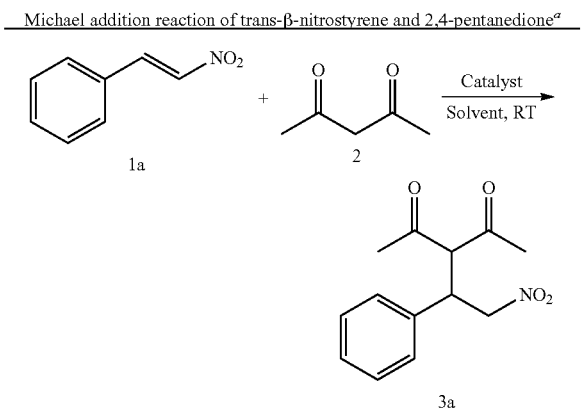

| Entry | Catalyst | Solvent | Time (min.) | Yield[b] (%) | Re-cyclable |
|---|---|---|---|---|---|
| 1 | KOH | $CH_2Cl_2$ | 40 | 55 | No |
| 2 | KOH | 2-MTHF[c] | 38 | 53 | No |

TABLE 1-continued

Michael addition reaction of trans-β-nitrostyrene and 2,4-pentanedione[a]

[Reaction scheme: 1a (styrene with NO2) + 2 (2,4-pentanedione) → Catalyst/Solvent, RT → 3a]

| Entry | Catalyst | Solvent | Time (min.) | Yield[b] (%) | Re-cyclable |
|---|---|---|---|---|---|
| 3 | KOH | H$_2$O | — | ND[d] | — |
| 4 | KOH | H$_2$O + CH$_2$Cl$_2$ | 60 | 25 | No |
| 5 | GO | CH$_2$Cl$_2$ | — | ND | — |
| 6 | GO | H$_2$O | — | ND | — |
| 7 | GO | H$_2$O + CH$_2$Cl$_2$ | — | ND | — |
| 8 | KOH + GO | CH$_2$Cl$_2$ | 37 | 59 | Yes |
| 9 | KOH + GO | H$_2$O | — | ND | Yes |
| 10 | KOH + GO | H$_2$O + CH$_2$Cl$_2$ | 10 | 83 | Yes |
| 11 | KOH + GO | H$_2$O + 2-MTHF | 10 | 82 | Yes |
| 12 | KOH + CE[e] | H$_2$O + CH$_2$Cl$_2$ | 30 | 76 | No |
| 13 | NaOH | CH$_2$Cl$_2$ | 45 | 45 | No |
| 14 | NaOH | H$_2$O | — | ND | — |
| 15 | NaOH | H$_2$O + CH$_2$Cl$_2$ | 60 | 15 | No |
| 16 | NaOH + GO | H$_2$O + CH$_2$Cl$_2$ | 15 | 75 | Yes |
| 17 | NaOH + CE | H$_2$O + CH$_2$Cl$_2$ | 45 | 41 | No |
| 18 | CsOH | CH$_2$Cl$_2$ | 30 | 60 | No |
| 19 | CsOH | H$_2$O | — | ND | — |
| 20 | CsOH | H$_2$O + CH$_2$Cl$_2$ | 60 | 23 | No |
| 21 | CsOH + GO | H$_2$O + CH$_2$Cl$_2$ | 10 | 80 | Yes |
| 22 | CsOH + CE | H$_2$O + CH$_2$Cl$_2$ | 30 | 55 | No |

[[a]Reactions were carried out with 1a (25 mg, 0.1676 mmol), 2 (1.5 equiv.), a base (KOH, NaOH or CsOH, 1.1 equiv.) 0.5 mg/mL aqueous graphene oxide (0.5 mL) and catalyst 18-crown-6-ether (1.1 equiv.).
[b]Isolated yield.
[c]2-Methyl tetrahydrofuran.
[d]Almost no product was detected.
[e]CE = 18-crown-6-ether.]

The catalytic properties of the graphene oxide were studied under various conditions including the use of different solvents and bases (Table 1). The same reactions using 18-crown-6-ether were also carried out for comparison. Control experiments included single-phase organic reactions using bases of differently sized metal ions without a phase transfer catalyst (Table 1, Entries 1, 2, 13 and 18), single-phase aqueous reactions without a phase transfer catalyst (Table 1, Entries 3, 14 and 19), and two-phase reactions without a phase transfer catalyst (Table 1, Entries 4, 15 and 20). No product was observed in the aqueous-only system (Table 1, Entries 3, 6, 9, 14 and 19), and also in the absence of bases (Table 1, Entries 5 to 7). But in the two-phase system in the absence of a phase transfer catalyst, the yield was poor, presumably owing to the poor transfer of OH$^-$ ions to the organic phase. For the control experiments using only one solvent system, the reaction of KOH+GO in only water did not produce any product. On the other hand, the reaction of KOH+GO in the methyl chloride solvent (Table 1, Entry 8) was slightly faster and produced 4% higher yield than that of KOH in the methyl chloride solvent (Table 1, Entry 1), but much lower than that of KOH+GO in the aqueous and methyl chloride two-phase solvent system (Table 1, Entry 10). As a result, the two-phase solvent system gives better yield and has shorter reaction time than the one-phase system (Table 1, Entries 8 to 10). The ability of graphene oxide to bind cations of various sizes was tested through a series of reactions using KOH, NaOH and CsOH (Table 1, Entries 10, 16 and 21); these were mirrored by experiments using 18-crown-6 ether (CE, crown ether) as a comparison phase transfer catalyst (Table 1, Entries 12, 17 and 22). When an aqueous graphene oxide solution (0.5 mL) was loaded with potassium cations using KOH, the reaction in the methyl chloride solution (1 mL) was completed within 10 minutes, affording the Michael addition reaction product in up to 83% yield rate (Table 1, Entry 10). The comparison reaction with crown ether was more than 3 times longer (30 min.), and gave poorer yield (Table 1, 76%, Entry 12). This difference was more pronounced when sodium hydroxide was used; graphene oxide yielded 75% and 18-crown-6 ether yielded 41% (Table 1, Entries 16 and 17). The yield of the reactions using the phase transfer catalyst including graphene oxide was nearly independent of the metal cation used: 83% for KOH, 75% for NaOH, and 80% for CsOH. This suggests that the metal cations were indeed intercalated between graphene oxide layers, as illustrated in FIG. 1. As expected, the crown ether catalyst performed best with the correctly sized K$^+$ cation (76% yield for KOH) and more poorly with the other two alkali bases (41% yield for NaOH and 55% yield for CsOH). However, even in the best case, crown ether did not perform well. The graphene oxide catalyst provided faster reactions and higher yields in all experiments. In this Example, the reactivity of graphene oxide, which was due to its hold on the cation, making the hydroxide base stronger in the organic phase, was observed. Furthermore, because the yield was high and the reaction was faster compared with those when using crown ether, this Example could conclude that individual graphene oxide sheets could carry more cations. This Example also used 2-methyl tetrahydrofuran (2-MTHF), which can replace methyl chloride in respect to greenery, as the organic solvent for the green reaction, instead of methyl chloride, and it acted similarly to methyl chloride (Table 1, Entries 2 and 11). The used graphene oxide could be easily recovered and reused by a simple process of filtering and washing with methyl chloride (Table 2).

TABLE 2

Recycling of a graphene oxide as a Michael addition reaction catalyst[a]

[Reaction scheme: 1a + 2 → KOH + GO / H$_2$O + CH$_2$Cl$_2$, RT → 3a]

| Cycle | Yield (%) | Cycle | Yield (%) | Cycle | Yield (%) |
|---|---|---|---|---|---|
| 1 | 83 | 4 | 82 | 7 | 77 |
| 2 | 81 | 5 | 80 | 8 | 78 |
| 3 | 80 | 6 | 79 | 9 | 76 |

[[a]All cycles were carried out with 1a (25 mg, 0.1676 mmol), 2 (1.5 equiv.), KOH (1.1 equiv.), and 0.5 mg/mL aqueous graphene oxide (0.5 mL) in methyl chloride.]

The recovered graphene oxide could be reused at least nine times almost without reduction of reaction yields. It is assumed that the recovered graphene oxide retained its catalytic activity due to the presence of many undamaged oxygen functional groups on the graphene oxide surface.

To further explore the methodology of this Example, this Example carried out related reactions using a series of trans-β-nitroolefin Michael acceptors, with a variety of substituents on the benzene ring including electron-donating groups such as methoxy and methyl, and electron-withdrawing halogen groups (F, Cl and Br). The final synthesis structure of the synthesized product was identified through hydrogen-nuclear magnetic resonance ($^1$H-NMR) (Table 3, FIG. 6 to FIG. 12). As summarized in Table 3, the graphene oxide system showed fairly good yields and short reaction times.

TABLE 3

Trans-β-Nitroolefins as Michael acceptors[a]

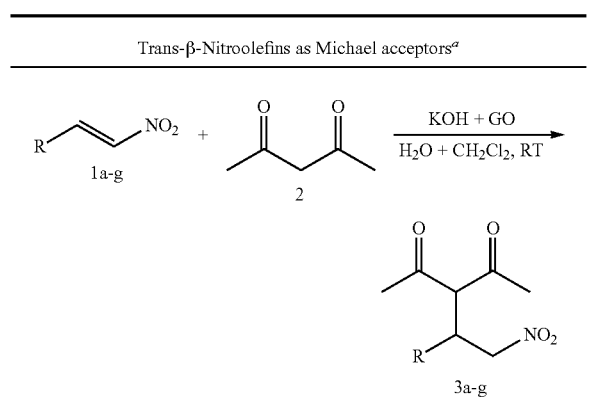

| Entry | R | Time(min.) | Yield[b](%) |
|---|---|---|---|
| 1 | phenyl (1a) | 10 | 83 |
| 2 | 4-methylphenyl (1b) | 16 | 80 |
| 3 | 4-methoxyphenyl (1c) | 16 | 77 |
| 4 | 4-fluorophenyl (1d) | 30 | 69 |
| 5 | 4-chlorophenyl (1e) | 23 | 79 |
| 6 | 4-bromophenyl (1f) | 25 | 73 |
| 7 | 2-thienyl (1g) | 20 | 78 |

[[a]Reactions were carried out with 1a-g (0.1676 mmol), 2 (1.5 equiv.), KOH (1.1 equiv.), and 0.5 mg/mL aqeous graphene oxide (0.5 mL) in methyl chloride (1 mL).
[b]Isolated yields.]

Next, this Example evaluated the scope of the reaction with a variety of 1,3-dicarbonyl compounds as Michael donors, with substituents including methyl, methoxyl, tert-butyl, and cycloolefins, and identified the final synthesis structure of the synthesized product through $^1$H-NMR (Table 4, FIG. 13 to FIG. 20).

TABLE 4

1,3-Dicarbonyl compounds as Michael donors[a]

Ph-CH=CH-NO$_2$ (1a) + R$^1$C(O)CHR$_2$C(O)R$^3$ (4a-4h) $\xrightarrow[\text{H}_2\text{O} + \text{CH}_2\text{Cl}_2, \text{RT}]{\text{KOH} + \text{CO}}$ 5a-h

| Entry | Product | Time (min.) | Yield[b] (%) |
|---|---|---|---|
| 1 | 5a | 35 | 80 |
| 2 | 5b | 2880 | 30 |
| 3 | 5c | 25 | 79 |
| 4 | 5d | 20 | 80 |
| 5 | 5e | 15 | 83 |
| 6 | 5f | 60 | 66 |
| 7 | 5g | 15 | 82 |

TABLE 4-continued 1,3-Dicarbonyl compounds as Michael donors[a]

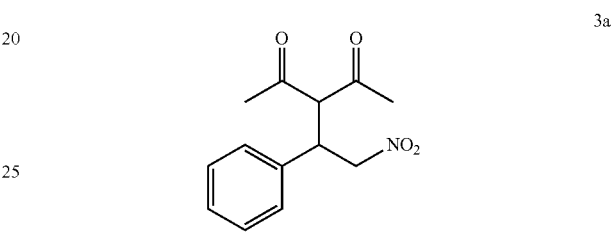

| Entry | Product | Time (min.) | Yield[b](%) |
|---|---|---|---|
| 8 | 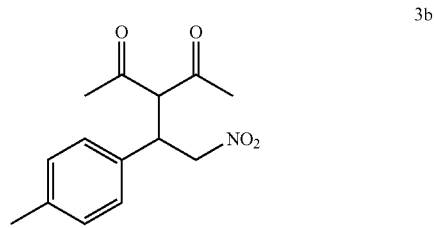 [SMILES: CC(=O)C(C(C)=O)C(C[N+](=O)[O-])c1ccc(C)cc1] | 25 | 81 |

[a]Reactions were carried out with 1a-g (25 mg, 0.1676 mmol), 4a-h (1.5 equiv.), KOH (1.1 equiv.), and 0.5 mg/mL aqueous graphene oxide (0.5 mL) in methyl chloride (1 mL).
[b]Isolated yields.]

Like the derivative Michael acceptors, most of the Michael donors showed fairly good yields and reasonable reaction times. According to the data of this Example, it can be suggested that oxygen functional groups in graphene oxide, including carbonyl, carboxylic, lactone, and quinone, and especially epoxy and hydroxyl groups, are responsible for interaction with the base cations, increasing the catalyst's ability to react strongly and quickly with reactants.

In summary, this Example has successfully demonstrated that graphene oxide sheets can be functioned as a phase transfer catalyst for the Michael addition reaction. As reactants, trans-β-nitrostyrene and 2,4-pentanedione and their derivatives were used, as well as differently sized alkali metal bases. The performance of graphene oxide, as the catalyst, was compared with 18-crown-6 ether, the conventional phase transfer catalyst. The graphene oxide promoted the formation of C—C bonds in the Michael addition reaction products, giving short reaction time and high yield compared with crown ether. The used phase transfer catalyst including graphene oxide could be recovered by simple filtering and washing and could be reused many times, while phase transfer catalysts such as crown ether are difficult to recover. Furthermore, the phase transfer catalyst including graphene oxide was effective with differently sized metal cation bases, while the crown ether catalyst worked effectively only with a specifically sized metal cation. And also, graphene oxide has the potential to provide an environmentally friendly, inexpensive and easy way to produce commercial products on a large scale. Thus, the phase transfer catalyst including graphene oxide provides a novel method for the formation of new C—C bonds, and can be used in an open system. This Example observed the graphene oxide's ability to provide the greatly enhanced phase transfer catalyst.

<Characterization of the Michael Addition Reaction Product>

A stereochemistry structure analysis for the product of the Michael addition reaction using the graphene oxide was conducted, and the following results were obtained (3a to 3g of Tables 1 and 3, and 5a to 5h of Table 4).

Configuration assignment: The structure of absolute stereochemistry was assigned as (R) by comparison of the retention time of HPLC with the literature data [H. Y. Bae, S. Some, J. S. Oh, Y. S. Lee and C. E. Song, Chem. Commun., 2011, 47, 9621-9623].

3a

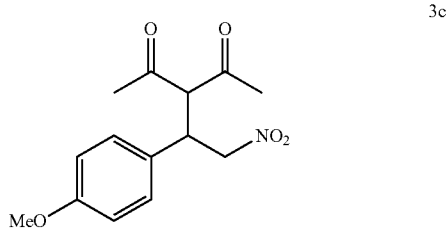 [SMILES: COc1ccc(C(C[N+](=O)[O-])C(C(C)=O)C(C)=O)cc1]

Purification by column chromatography (4:1=Hexane:EtOAc) afforded 3a as a white solid (83% yield). Analytical data was matched with previously reported values.

$^1$H NMR (300 MHz, CDCl$_3$, Me$_4$Si): δ 7.26-7.19 (m, 3H), 7.12-7.10 (m, 2H), 4.58-4.55 (m, 2H), 4.30 (d, 1H, J=10.5 Hz), 4.21-4.17 (m, 1H), 2.23 (s, 3H), 1.87 (s, 3H); HPLC (AD-H, Hexane:iPrOH=90:10, 1.0. mL/min, 220 nm): t$_{major}$=10.5 min, t$_{minor}$=14.1 min; ~7% ee.

3b

Purification by column chromatography (4:1=Hexane:EtOAc) afforded 3b as a white solid (80% yield). Analytical data was matched with previously reported values.

$^1$H NMR (300 MHz, CDCl$_3$, Me$_4$Si): δ 7.20-6.97 (m, 4H), 4.54-4.52 (m, 2H), 4.28 (d, J=10.8 Hz, 1H), 4.17-4.11 (m, 1H), 2.22 (s, 3H), 2.19 (s, 3H), 1.86 (s, 3H)

3c

Purification by column chromatography (4:1=Hexane:EtOAc) afforded 3c as a white solid (77% yield). Analytical data was matched with previously reported values.

¹H NMR (300 MHz, CDCl₃, Me₄Si): δ 7.03 (d, J=8.7 Hz, 3H), 6.76 (d, 3J=8.7 Hz, 2H), 4.53-4.51 (m, 2H), 4.23 (d, J=11.1 Hz, 1H), 4.16-4.08 (m, 1H), 3.69 (s, 3H), 2.19 (s, 3H), 1.86 (s, 3H)

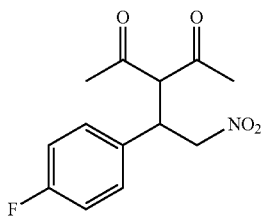
3d

Purification by column chromatography (4:1=Hexane:EtOAc) afforded 3d as a white solid (69% yield). Analytical data was matched with previously reported values.

¹H NMR (300 MHz, CDCl₃, Me₄Si): δ 7.13-7.09 (m, 2H), 6.97-6.91 (m, 2H), 4.58-4.49 (m, 2H), 4.27 (d, J=10.8, 1H), 4.21-4.13 (m, 1H), 2.20 (s, 3H), 1.89 (s, 3H)

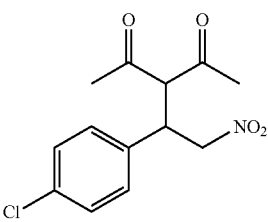
3e

Purification by column chromatography (4:1=Hexane:EtOAc) afforded 3e as a white solid (79% yield). Analytical data was matched with previously reported values.

¹H NMR (300 MHz, CDCl₃, Me₄Si): δ 7.23 (d, J=8.4 Hz, 2H), 7.07 (d, J=8.4 Hz, 2H), 4.55 (d, J=6.3 Hz, 2H), 4.14 (d, J=10.5 Hz, 1H), 4.20-4.12 (m, 1H), 2.20 (s, 3H), 1.90 (s, 3H)

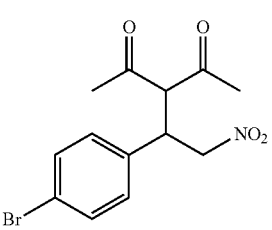
3f

Purification by column chromatography (4:1=Hexane:EtOAc) afforded 3f as a white solid (75% yield). Analytical data was matched with previously reported values.

¹H NMR (300 MHz, CDCl₃, Me₄Si): δ 7.46 (d, J=8.4 Hz, 2H), 7.08 (d, J=8.4 Hz, 2H), 4.62 (d, J=6.3 Hz, 2H), 4.25 (d, J=6.0 Hz, 1H), 4.26-4.18 (m, 1H), 2.29 (s, 3H), 1.98 (s, 3H)

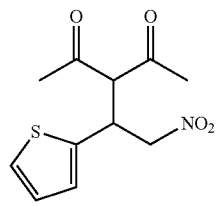
3g

Purification by column chromatography (4:1=Hexane:EtOAc) afforded 3g as a white solid (78% yield). Analytical data was matched with previously reported values.

¹H NMR (300 MHz, CDCl₃, Me₄Si): δ 7.28-7.23 (m, 1H), 6.93-6.89 (m, 2H), 4.68-4.66 (m, 2H), 4.58-4.51 (m, 1H), 4.40 (d, J=9.9 Hz, 1H), 2.29 (s, 3H), 2.07 (s, 3H)

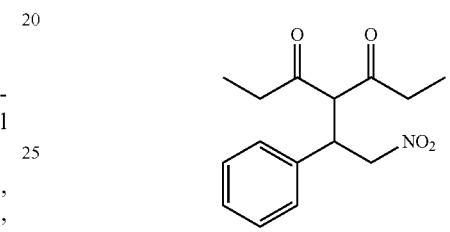
5a

Purification by column chromatography (5:1=Hexane:Acetone) afforded 5a as a white solid (80% yield). Analytical data was matched with previously reported values.

¹H NMR (300 MHz, CDCl₃, Me₄Si): δ 7.32-7.27 (m, 3H), 7.18-7.15 (m, 2H), 4.71-4.60 (m, 2H), 4.35-4.23 (m, 2H), 2.65-2.44 (m, 2H), 2.38-2.25 (m, 1H), 2.20-2.04 (m, 1H), 1.07 (t, J=7.2 Hz, 3H), 0.78 (t, J=7.2 Hz, 3H)

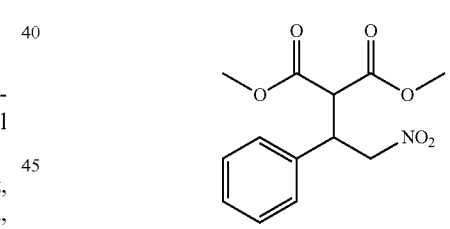
5b

Purification by column chromatography (4:1=Hexane:EtOAc) afforded 5b as a white solid (50% yield). Analytical data was matched with previously reported values.

¹H NMR (300 MHz, CDCl₃, Me₄Si): δ 7.33-7.21 (m, 5H), 4.96-4.83 (m, 2H), 4.24 (td, J=8.8, 5.7 Hz, 1H), 3.86 (d, J=9.2 Hz, 1H), 3.76 (s, 3H), 3.56 (s, 3H)

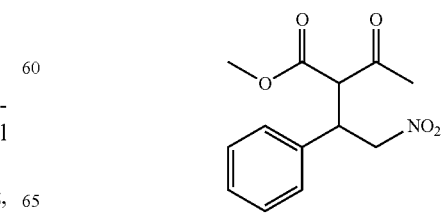
5c

Purification by column chromatography (4:1=Hexane:EtOAc) afforded 5c as a white solid (79% yield, 1:1 mixture of diastereomers). Analytical data was matched with previously reported values.

$^1$H NMR (300 MHz, CDCl$_3$, Me$_4$Si): δ 7.33-7.25 (m, 3H), 7.21-7.18 (m, 2H), 4.83-4.81 (m, 1H), 4.78-4.76 (m, 1H), 4.29-4.17 (m, 1H), 4.12 (d, J=9.6 Hz, 0.5H), 4.03 (d, J=9.6 Hz, 0.5H), 3.77-3.53 (s, 3H), 2.29-2.05 (s, 3H); dr=1:1 (determined by integration of $^1$H NMR)

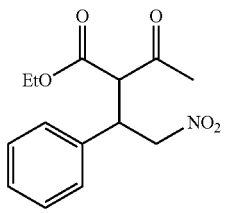

5d

Purification by column chromatography (5:1=Hexane:Acetone) afforded 5d as a white solid. Analytical data was matched with previously reported values (80% yield, 1.5:1 mixture of diastereomers).

$^1$H NMR (300 MHz, CDCl$_3$, Me$_4$Si): δ 7.32-7.27 (m, 3H), 7.22-7.19 (m, 2H), 4.89-4.76 (m, 2H), 4.26-4.18 (m, 2H), 4.12 (d, J=9.9 Hz, 0.6H) 4.03 (d, 0.4 H, J=9.9 Hz), 3.96 (q, 1H, J=7.2 Hz), 2.30-2.05 (s, 3H), 1.28-1.00 (t, J=7.2 Hz, 4H); dr=1.5:1 (determined by integration of $^1$H NMR)

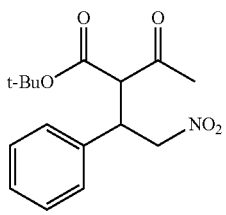

5e

Purification by column chromatography (4:1=Hexane:EtOAc) afforded 5e as a white solid (83% yield, 4.9:1 mixture of diastereomers). Analytical data was matched with previously reported values.

$^1$H NMR (300 MHz, CDCl$_3$, Me$_4$Si): δ 7.34-7.29 (m, 3H), 7.25-7.20 (m, 2H), 4.85-4.82 (m, 0.4H), 4.77-4.65 (m, 2H), 4.23-4.10 (m, 1H), 4.03 (d, J=10.2 Hz, 0.83H), 3.92 (d, J=10.2 Hz, 0.17H), 2.30-2.06 (s, 3H), 1.47-1.11 (s, 9H)

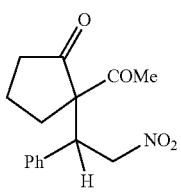

5f

Purification by column chromatography (4:1=Hexane:EtOAc) afforded 5f as a white solid (66% yield, 7.3:1 mixture of diastereomers). Analytical data was matched with previously reported values.

$^1$H NMR (300 MHz, CDCl$_3$, Me$_4$Si): δ 7.24-7.34 (m, 5H), 5.01 (dd, J=11.1, 13.2 Hz, 0.12H) 4.86 (dd, J=11.4 Hz and J=13.5 Hz, 0.88H), 4.60-4.51 (dd, J=3.9 Hz and 13.2 Hz, 1H), 4.39-4.28 (dd, J=3.9 and J=11.1 Hz, 1H), 2.61-2.54 (m, 1H), 2.33 (s, 3H), 2.26-2.14 (m, 1H), 2.03-1.93 (m, 1H), 1.80-1.65 (m, 3H); dr=7.3:1 (determined by integration of $^1$H NMR)

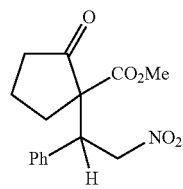

5g

Purification by column chromatography (4:1=Hexane:EtOAc) afforded 5g as a colorless oil (82% yield, 99:1 mixture of diastereomers). Analytical data was matched with previously reported values.

$^1$H NMR (300 MHz, CDCl$_3$, Me$_4$Si): δ 7.31-7.23 (m, 5H), 5.17 (dd, J=4.2 and 13.5 Hz, 1H), 5.01 (dd, J=10.8 Hz and J=13.5 Hz, 1H), 4.08 (dd, J=3.9 Hz and 10.8 Hz, 1H), 3.75 (s, 3H), 2.40-2.32 (m, 2H), 2.05-1.82 (m, 4H); dr>99:1 (determined by integration of $^1$H NMR)

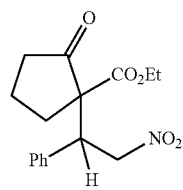

5h

Purification by column chromatography (4:1=Hexane:EtOAc) afforded 5h as a colorless oil (81% yield, 99:1 mixture of diastereomers). Analytical data was matched with previously reported values.

$^1$H NMR (300 MHz, CDCl$_3$, Me$_4$Si): δ 7.34-7.27 (m, 5H), 5.18 (dd, J=3.9 and 13.6 Hz, 1H), 5.01 (dd, J=10.9 and 13.5 Hz, 1H), 4.24-4.17 (m, 1H), 4.08 (dd, J=3.9 and 10.9 Hz, 1H), 2.40-2.32 (m, 2H), 2.07-1.74 (m, 4H), 1.27 (t, J=7.1 Hz, 1H); dr >99:1 (determined by integration of $^1$H NMR)

In the products of the Michael addition reaction, mirror enantiomeric selective properties of the product using graphene oxide, the product treated with crown ether, and the only base treated product were studied.

Figure 21:
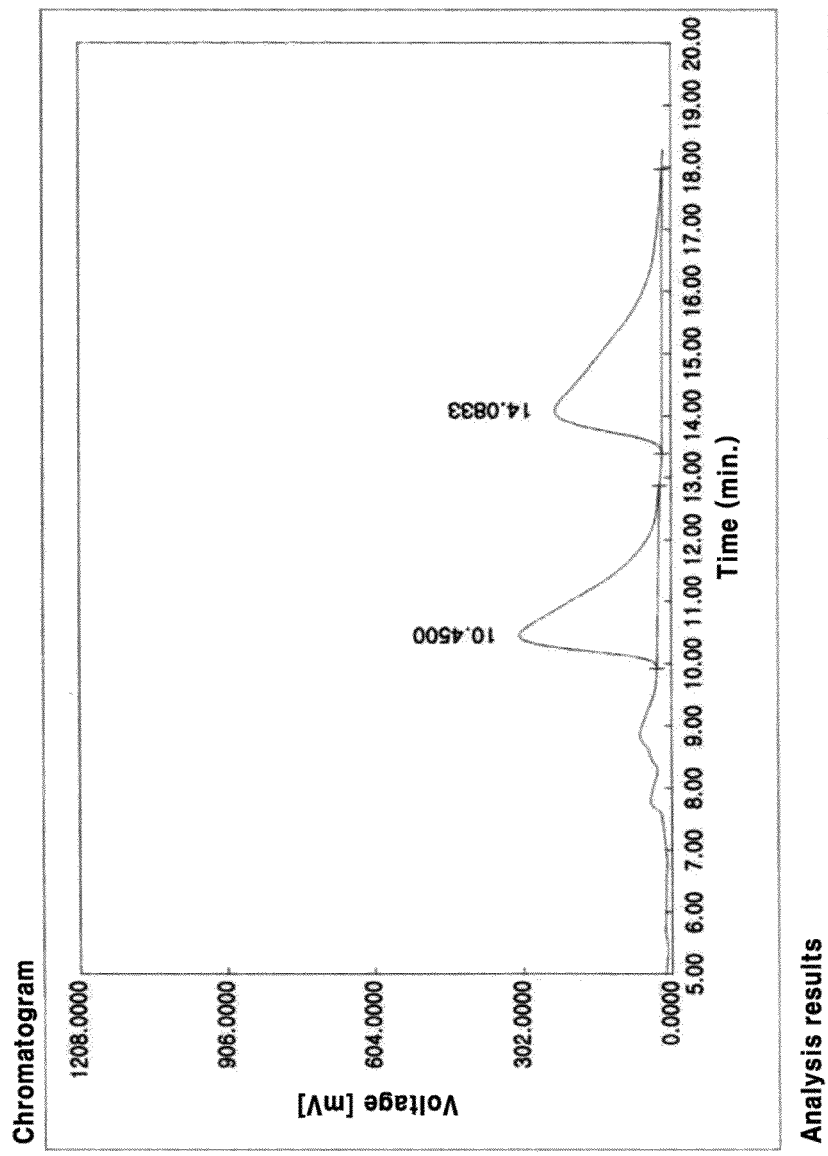
FIG. 21 is a chromatogram graph of a product of Michael addition reaction using an example of a phase transfer catalyst including a graphene oxide in accordance with the present disclosure.
Figure 22:
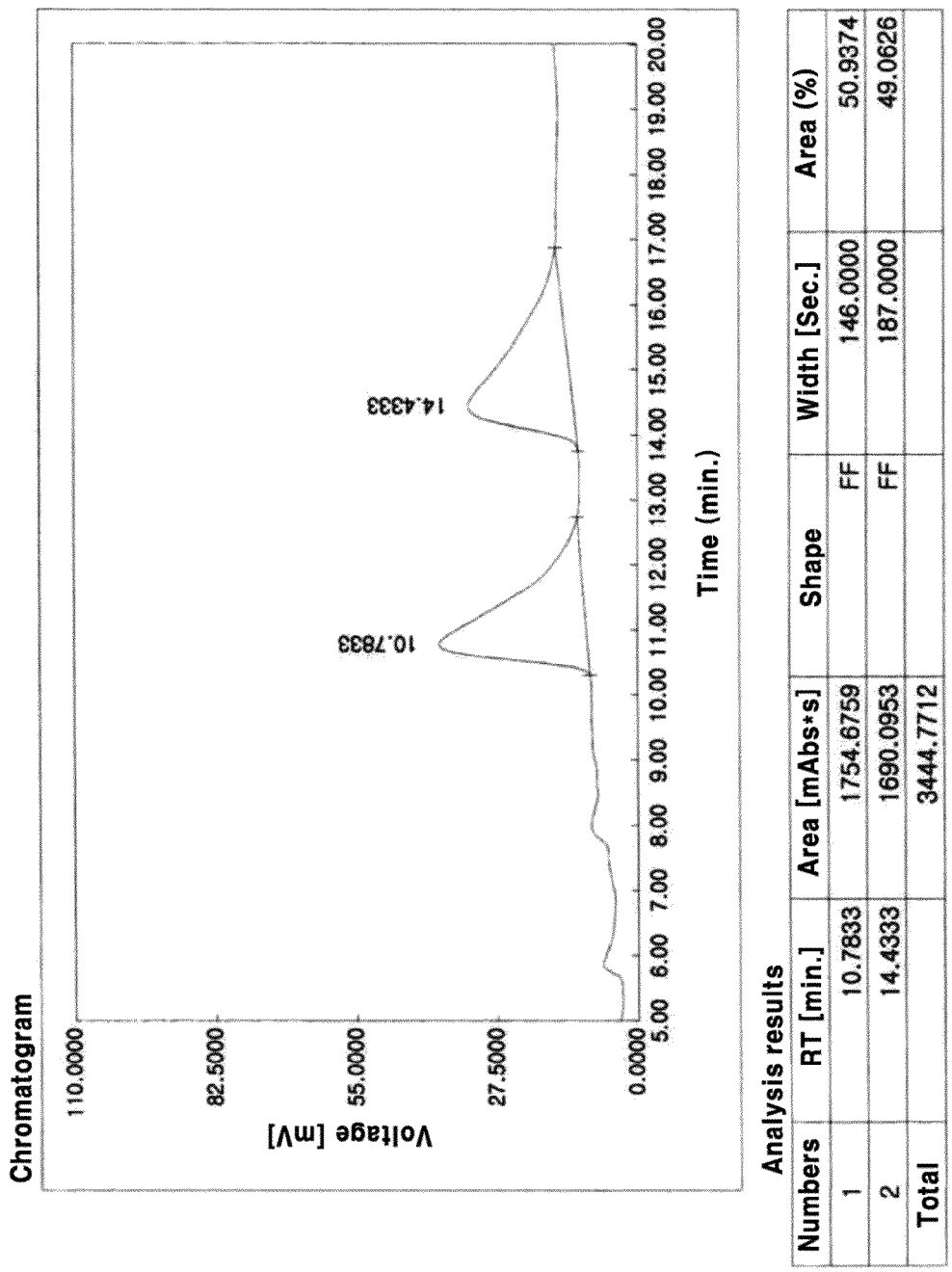
FIG. 22 is a chromatogram graph of a product of Michael addition reaction using crown ether and only one base in accordance with the present disclosure.

Enantiomeric selective property of the product 3a with the graphene oxide phase transfer catalyst (Tables 1 and 3), and it showed approximately 7% mirror enantiomeric excess (FIG. 21). The crown ether phase transfer catalyst product and the only base treated product were racemic in comparison to the graphene oxide phase transfer catalyst product (FIG. 22). The 2D template structure of the graphene oxide helps to get an enantiomerically selective product even though the ee value is not high. Now this current work is focused on improving the yield and enantiomeric selectivity of the graphene oxide phase transfer catalyst product.

<Carrying Out the Aldol Condensation Reaction>

Graphene oxide (GO) was dispersed in deionized water to make a concentration of 0.5 mg/mL, and sodium methoxide (59.4 mg, 1.1 equiv.) was added as a base to 0.5 mL of the graphene oxide solution. Subsequently, the graphene oxide solution, to which sodium methoxide was added, was added to a mixture of a methyl chloride (MC) solution (1 mL), which included reactants in a 5 ml vial and acetaldehyde (88 mg, 2.0 mmol). The methyl chloride solution, which included the reactants, the graphene oxide and the base, was vigorously stirred by using one magnetic bar at a stirring speed of 900 rpm at a room temperature so that 3-hydroxybuthanal was obtained.

<Carrying Out the Claisen Condensation Reaction>

Graphene oxide (GO) was dispersed in deionized water to make a concentration of 0.5 mg/mL, and potassium hydroxide (61.6 mg, 1.1 equiv.) was added as a base to 0.5 mL of the graphene oxide solution. Subsequently, the graphene oxide solution, to which potassium hydroxide was added, was added to 1 mL methyl chloride (MC) solution, which included reactants in a 5 mL vial, butan-2-one (72 mg, 1.0 mmol) and methyl acetate (74 mg, 1.0 mmol). The methyl chloride solution, which included the reactants, the graphene oxide and the base, was vigorously stirred by using one magnetic bar at a stirring speed of 900 rpm at a room temperature so that 3-methylpentane-2,4-dione was obtained.

<Carrying Out the Perkin Reaction>

Graphene oxide (GO) was dispersed in deionized water to make a concentration of 0.5 mg/mL, and potassium hydroxide (61.6 mg, 1.1 equiv.) was added as a base to 0.5 mL of the graphene oxide solution. Subsequently, the graphene oxide solution, to which potassium hydroxide was added, was added to 1 mL of a methyl chloride (MC) solution, which included reactants in a 5 mL vial, benzaldehyde (106 mg, 1.0 mmol) and acetic anhydride (102 mg, 1.0 mmol). The methyl chloride solution, which included the reactants, the graphene oxide and the base, was vigorously stirred by using one magnetic bar at a stirring speed of 900 rpm at a room temperature so that cinnamic acid was obtained.

Provided above are various example embodiments related to a phase transfer catalyst for an addition or condensation organic reaction that is suitable for use in the presence of a base catalyst including an alkali metal ion or alkali earth metal ion. Also provided above are various example embodiments related to a method of using such a phase transfer catalyst. In one example, the phase transfer catalyst includes a graphene oxide containing an oxygen functional group, and the addition or condensation organic reaction is promoted by bonding the oxygen functional group with the alkali metal ion or alkali earth metal ion during the addition or condensation organic reaction. However, the present disclosure is not limited thereto.

In one example embodiment, there is provided a phase transfer catalyst for an addition or condensation organic reaction in the presence of a basic catalyst including an alkali metal ion or alkali earth metal ion, in which the phase transfer catalyst includes a graphene oxide containing an oxygen functional group that may be substantially uniformly dispersed in an aqueous phase comprising an aqueous solvent, and in which the addition or condensation organic reaction is promoted by bonding the oxygen functional group with the alkali metal ion or alkali earth metal ion during the addition or condensation organic reaction so as to facilitate the transfer of the alkali metal ion or alkali earth metal ion into an organic phase comprising an organic solvent. However, the present disclosure is not limited thereto.

In accordance with one example embodiment, it is possible to provide a simple and environment-friendly production process for obtaining a product of an addition or condensation organic reaction and its derivatives by using the phase transfer catalyst including a graphene oxide. As a catalyst for the organic reaction, the graphene oxide can reduce reaction time and provide high yield, compared to 18-crown-6 ether, which is a conventional phase transfer catalyst. Since in the organic reaction, the used phase transfer catalyst including graphene oxide could be recovered by simple filtering and washing, and could be reused many times while rarely reducing reaction yield, it is economical. The phase transfer catalyst including a graphene oxide could be effective for holding differently sized metal cations. However, the present disclosure is not limited thereto.

The phase transfer catalyst including a graphene oxide provides a novel method for formation of new C—C bonds, and can be used in an open system. The phase transfer catalyst including a graphene oxide has the potential to provide an environmentally friendly, inexpensive and easy way to produce commercial products on a large scale.

The above description of the example embodiments is provided for the purpose of illustration, and it would be understood by those skilled in the art that various changes and modifications may be made without changing technical conception and essential features of the example embodiments. Thus, it is clear that the above-described example embodiments are illustrative in all aspects and do not limit the present disclosure. For example, each component described to be of a single type can be implemented in a distributed manner. Likewise, components described to be distributed can be implemented in a combined manner.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

We claim:

1. A catalyst for an addition or condensation reaction, the catalyst comprising:
    a graphene oxide comprising an oxygen functional group; and, an alkali metal ion or alkali earth metal ion.

2. The catalyst of claim 1,
    wherein the catalyst is a phase transfer catalyst capable of being recovered after the addition or condensation reaction and then being reused.

3. The catalyst of claim 1,
    wherein the oxygen functional group comprises a member selected from the group consisting of an epoxy group, a hydroxyl group, a carbonyl group, a carboxyl group, and combinations thereof.

4. The catalyst of claim 1,
    wherein the alkali metal ion or alkali earth metal ion is a cation of a metal selected from the group consisting of sodium, potassium, cesium, rubidium, calcium, strontium, barium, and combinations thereof.

5. The catalyst of claim 1,
    wherein the addition or condensation reaction is a Michael addition reaction, an Aldol condensation reaction, a Claisen condensation reaction, or a Perkin reaction.

6. The catalyst of claim 5,
wherein the Michael addition reaction is performed by adding a Michael acceptor compound and a Michael donor compound.

7. The catalyst of claim 6,
wherein the Michael donor compound is represented by the following Formula (1):

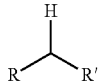

Formula (1)

wherein R or R' is each independently a $C_{1-12}$ alkyl group, a $C_{3-12}$ allyl group, a $C_{3-12}$ cycloalkyl group, a $C_{6-12}$ aryl group, a $C_{7-18}$ aralkyl group, a cyano group, a nitro group, an epoxide group, or a carbonyl group.

8. The catalyst of claim 6,
wherein the Michael acceptor compound is a member selected from the group consisting of an α, β-unsaturated carbonyl compound, an α, β-unsaturated nitrile compound, and combinations thereof.

* * * * *